(12) United States Patent
Tsuboyama et al.

(10) Patent No.: US 7,834,135 B2
(45) Date of Patent: Nov. 16, 2010

(54) LIGHT EMITTING DEVICE AND POLYMERIC MIXED-METAL COMPLEX

(75) Inventors: Akira Tsuboyama, Machida (JP); Kazunori Ueno, Ebina (JP); Yoichi Sasaki, Sapporo (JP); Kiyoshi Tsuge, Sapporo (JP); Seiko Shibata, Hino (JP); Motoshi Tamura, Ikeda (JP)

(73) Assignee: Canon Kabushiki Kaisha, Tokyo (JP)

( * ) Notice: Subject to any disclaimer, the term of this patent is extended or adjusted under 35 U.S.C. 154(b) by 77 days.

(21) Appl. No.: 11/847,703

(22) Filed: Aug. 30, 2007

(65) Prior Publication Data

US 2008/0058498 A1    Mar. 6, 2008

(30) Foreign Application Priority Data

Sep. 6, 2006    (JP)    .............................. 2006-241147

(51) Int. Cl.
*C08G 79/00*    (2006.01)
(52) U.S. Cl. ..................................... 528/395
(58) Field of Classification Search ................. 528/395
See application file for complete search history.

(56) References Cited

U.S. PATENT DOCUMENTS

| 3,483,142 | A | * | 12/1969 | Saraceno | ........................ | 528/9 |
| 3,483,143 | A | * | 12/1969 | Saraceno et al. | ............. | 528/271 |
| 4,185,043 | A | * | 1/1980 | Shaffer | ........................ | 525/364 |
| 4,960,835 | A | * | 10/1990 | Towle et al. | ................. | 525/389 |
| 5,681,659 | A | * | 10/1997 | Shi et al. | .................... | 428/480 |
| 6,124,427 | A | * | 9/2000 | Atwood | ........................ | 528/485 |
| 7,232,618 | B2 | | 6/2007 | Yamada et al. | ............... | 428/690 |
| 7,238,435 | B2 | * | 7/2007 | Kamatani et al. | ............ | 428/690 |
| 7,279,233 | B2 | | 10/2007 | Tsuboyama et al. | .......... | 428/690 |
| 7,413,818 | B2 | * | 8/2008 | Tsuboyama et al. | .......... | 428/690 |
| 2005/0079384 | A1 | * | 4/2005 | Tsuboyama et al. | .......... | 428/690 |
| 2006/0202197 | A1 | * | 9/2006 | Nakayama et al. | ............ | 257/40 |
| 2006/0280968 | A1 | | 12/2006 | Kamatani et al. | ............ | 428/690 |
| 2007/0072001 | A1 | | 3/2007 | Tsuboyama et al. | .......... | 428/690 |
| 2007/0190358 | A1 | * | 8/2007 | Byun et al. | ................... | 428/690 |
| 2007/0207344 | A1 | * | 9/2007 | Kamatani et al. | ............ | 428/690 |
| 2007/0212570 | A1 | * | 9/2007 | Kamatani et al. | ............ | 428/690 |
| 2007/0216294 | A1 | * | 9/2007 | Kamatani et al. | ............ | 313/506 |
| 2007/0292717 | A1 | | 12/2007 | Watanabe et al. | ............ | 428/690 |
| 2008/0100212 | A1 | * | 5/2008 | Tsuboyama et al. | .......... | 313/504 |

OTHER PUBLICATIONS

Araki et al., "Luminescence Ranging from Red to Blue: A Series of Copper(I)-Halide Complexes Having Rhombic $\{Cu_2(\mu-X)_2\}$ (X=BR and I) Units with *N*-Heteroaromatic Ligands," *Inorg. Chem.*, No. 44, 9667-9675 (2005).
"Proceedings 3F1-14 of the 86th Spring Annual Meeting of the Chemical Society of Japan" (2006).

* cited by examiner

*Primary Examiner*—Mark Eashoo
*Assistant Examiner*—Liam J Heincer
(74) *Attorney, Agent, or Firm*—Fitzpatrick, Cella, Harper & Scinto

(57) ABSTRACT

To provide a light emitting device capable of emitting light with high efficiency and of being formed by a coating process, the present invention provides a light emitting device including as a light emitting material a polymeric mixed-metal complex containing two or more kinds of metals selected from Cu, Ag, and Au.

2 Claims, 9 Drawing Sheets

LIGHT EMITTING DEVICE AND POLYMERIC MIXED-METAL COMPLEX

BACKGROUND OF THE INVENTION

1. Field of the Invention

The present invention relates to a metal complex using a copper group metal, and more specifically, to a polymeric mixed-metal complex containing plural metals out of copper, silver, and gold. In addition, the present invention relates to a light emitting device using the polymeric mixed-metal complex as a light emitting material.

2. Description of the Related Art

Conventional examples of a polymeric complex using a copper group metal include copper polymeric complexes listed in "Luminescence Ranging from Red to Blue: A Series of Copper(I)-Halide Complexes Having Rhombic $\{Cu_2(\mu\text{-}X)_2\}$ (X=Br and I) Units with N-Heteroaromatic Ligands (Araki, H.; Tsuge, K.; Sasaki, Y.; Ishizaka, S.; Kitamura, N Inorg. Chem.; (Article); 2005; 44 (26); 9667-9675.)". Specific examples of such copper polymeric complexes include those each having a structural formula shown in the following formula (10).

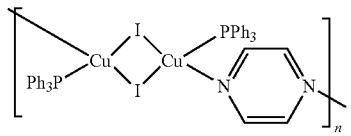

(10)

A polymeric metal complex described in the above document emits light in a visible light region, and its luminescent color can be selected by properly selecting a ligand. However, the complex uses only copper as a metal.

Meanwhile, "Proceedings 3F1-14 of the 86th spring annual meeting of the Chemical Society of Japan (2006) "Synthesis and light emitting property of each of gold(I)-silver(I) mixed-metal complex and copper(I)-silver(I) mixed-metal complex each using dimercaptothiadiazole as crosslinking ligand" by Motoshi Tamura, Kota Suzuki, Kiyoshi Tsuge, Yoichi Sasaki, Shoji Ishizaka, and Noboru Kitamura" describe a polymeric mixed-metal complex represented by the following structural formula.

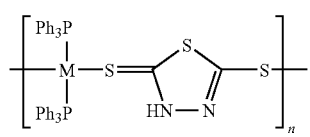

(11)

The above document describes that the mixed-metal complex is synthesized by selecting two kinds from Cu, Ag, and Au as M, and describe the light emitting property of the mixed-metal complex.

However, none of the documents describes the application of each of those complexes to a light emitting material for use in a light emitting device, and the contents of the documents are limited to researches on the molecular structures and photophysical properties of the complexes.

SUMMARY OF THE INVENTION

In view of the foregoing, an object of the present invention is to provide a light emitting device capable of emitting light with high efficiency.

According to the present invention, there is provided a light emitting device including, as a light emitting material, a polymeric mixed-metal complex containing two or more kinds of metals selected from Cu, Ag, and Au.

In addition, according to the present invention, there is provided a polymeric mixed-metal complex represented by the following general formula (3):

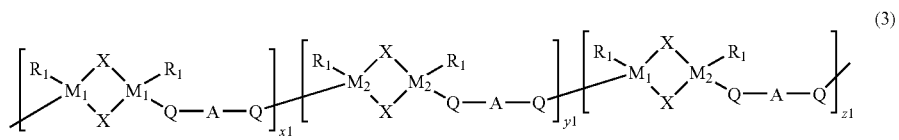

(3)

where $M_1$ and $M_2$ represent different metals, and are each selected from Cu, Ag, and Au.

$R_1$ represents a monodentate ligand using one of an N atom and a P atom as a coordinating atom; X is selected from halogen atoms Cl, Br, and I; and Q-A-Q represents a bidentate ligand using Q as a coordinating atom, Q is chosen from N and P, and two Q atoms are bonded to each other by A formed of plural covalent bonds.

x1, y1, and z1 each represent the number of repeating structures, an arrangement of the repeating structures may be one of a regular arrangement and an irregular arrangement, and x1, y1, and z1 satisfy a relationship of $50<(x1+y1+z1)<1,000,000$.

A complex of the present invention can stably emit light with high efficiency at room temperature. Therefore, a light emitting device using the complex can emit light with high efficiency.

Further features of the present invention will become apparent from the following description of exemplary embodiments with reference to the attached drawings.

DESCRIPTION OF THE EMBODIMENTS

Figure 1:
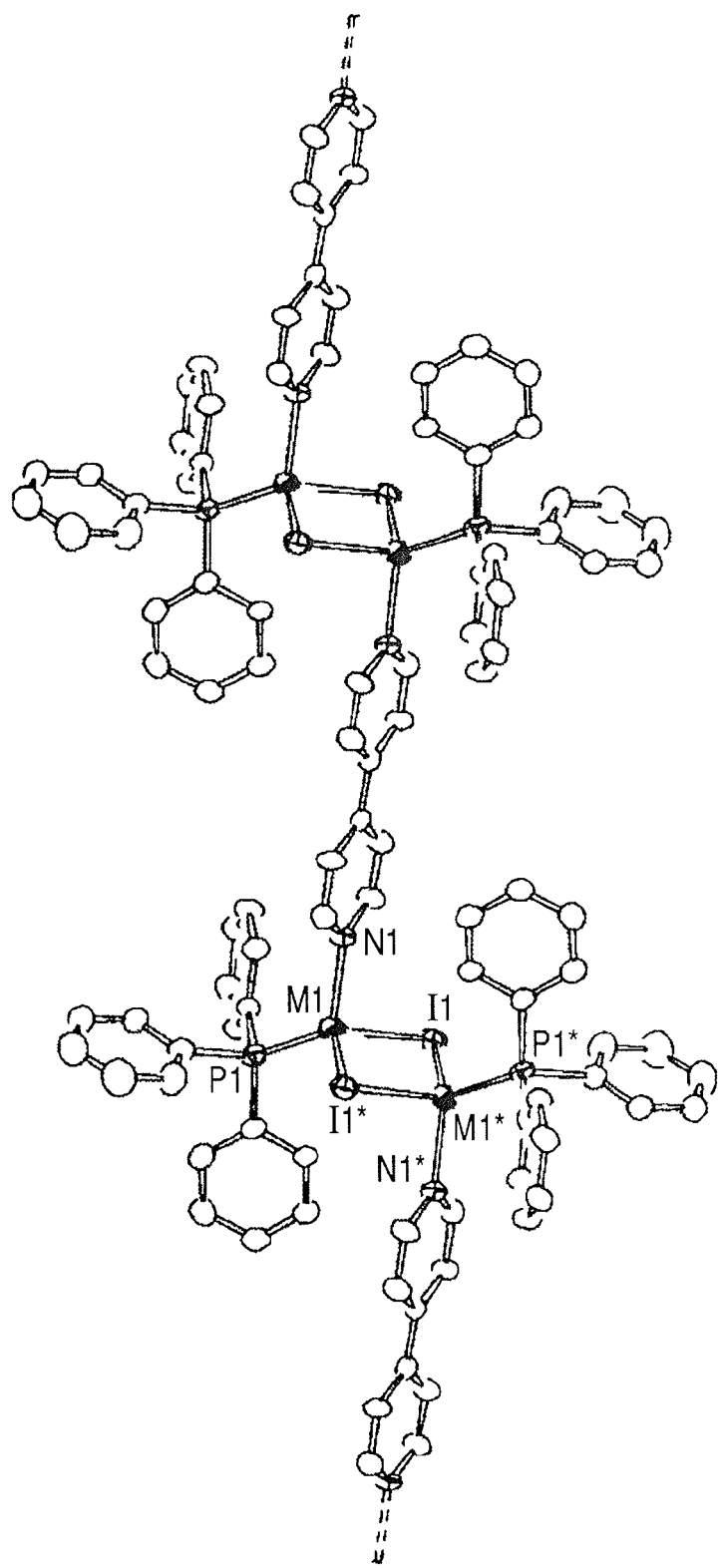
FIG. 1 is an ORTEP view of $[\{(Cu_xAg_{1-x})_2I_2(PPh_3)_2\}(bpy)]_n$ (x=0.5).

The inventors of the present invention have paid attention to a polymeric mixed-metal complex, and have made investigation on the application of the complex to a light emitting material. The term "polymeric mixed-metal complex" refers to a polymeric compound having a metal complex structure in any one of its repeating units, and containing two or more kinds of metals.

The inventors of the present invention have made investigation with a view to improving the light emitting property of a conventional polymeric copper complex and applying the complex to a light emitting device in view of the fact that the complex emits light having relatively high intensity. The points to consider in the investigation are (1) a emission wavelength (emission spectrum),
(2) an emission lifetime, and
(3) stability.

With regard to the investigation, the inventors of the present invention have paid attention to a metal of a complex. The inventors have designed and synthesized a polymeric mixed-metal complex by mixing metals, that is, two or more of copper, silver, and gold in the same group as that of copper, and have investigated an influence of a ratio between the metals on the light emitting property of the resultant complex. What is important in designing a polymeric mixed-metal complex is that the respective single metal complexes serving as bases must have nearly identical structures. The metal complexes of copper, silver, and gold each have a coordination number of 2, 3, 4, or the like. The production of a polymeric mixed-metal complex as a result of the mixing of the metal complexes of copper, silver, and gold requires the selection of a ligand allowing those metal complexes to have nearly identical structures.

The polymeric mixed-metal complex which can preferably be used in the present invention is represented by one of the following general formulae (1) and (2):

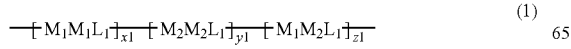

(1)

wherein $M_1$ and $M_2$ represent different metals, and are each selected from Cu, Ag, and Au; L1 represents a ligand group including an organic compound ligand; $M_1M_1L_1$, $M_2M_2L_1$, and $M_1M_2L_1$ each represent a repeating unit having a dinuclear complex structure; x1 represents the number of the repeating units $M_1M_1L_1$, y1 represents the number of the repeating units $M_2M_2L_1$, and z1 represents the number of the repeating units $M_1M_2L_1$; an arrangement of $M_1M_1L_1$, $M_2M_2L_1$, and $M_1M_2L_1$ may be one of a regular arrangement and an irregular arrangement; and x1, y1, and z1 satisfy a relationship of 50<(x1+y1+z1)<1,000,000;

(2)

wherein $M_1$ and $M_2$ represent different metals, and are each selected from Cu, Ag, and Au; $L_2$ represents a ligand group including an organic compound ligand; $M_1L_2$ and $M_2L_2$ each represent a repeating unit having a mononuclear complex structure; x2 represents the number of the repeating units $M_1L_2$ and y2 represents the number of the repeating units $M_2L_2$, an arrangement of $M_1L_2$ and $M_2L_2$ may be one of a regular arrangement and an irregular arrangement; and x2 and y2 satisfy a relationship of 50<(x2+y2)<1,000,000.

A complex represented by the following general formula (3) is preferably used as the complex represented by the general formula (1), and a complex represented by the following general formula (4) is more preferably used as the complex represented by the general formula (1):

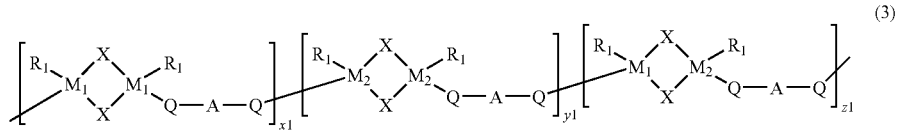

(3)

wherein: $R_1$ represents a monodentate ligand using one of an N atom and a P atom as a coordinating atom;

X is selected from halogen atoms Cl, Br, and I; and Q-A-Q represents a bidentate ligand using Q as a coordinating atom, Q is chosen from N and P, and two Q atoms are bonded to each other by A formed of plural covalent bonds;

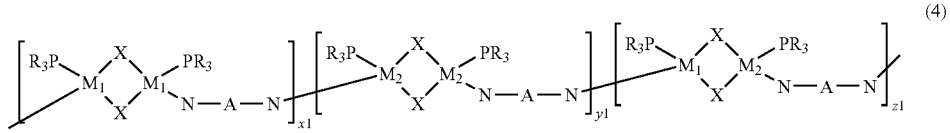

(4)

wherein $PR_3$ represents a tertiary phosphine using P as a coordinating atom, and is selected from tertiary phosphines shown in the following structural formulae (5):

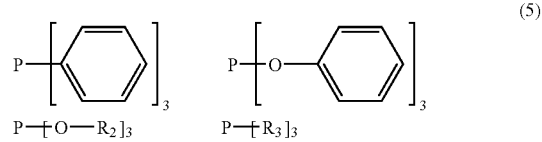

(5)

wherein: a hydrogen atom of a phenyl group may be substituted by one of a halogen atom, a branched or linear alkyl group having 6 or less carbon atoms, and a branched or linear alkoxyl group having 6 or less carbon atoms, and $R_2$ and $R_3$ each represent a linear, branched, or cyclic alkyl group having 6 or less carbon atoms.

In the general formula (4), N-A-N is preferably selected from the following structural formulae (6):

(6)

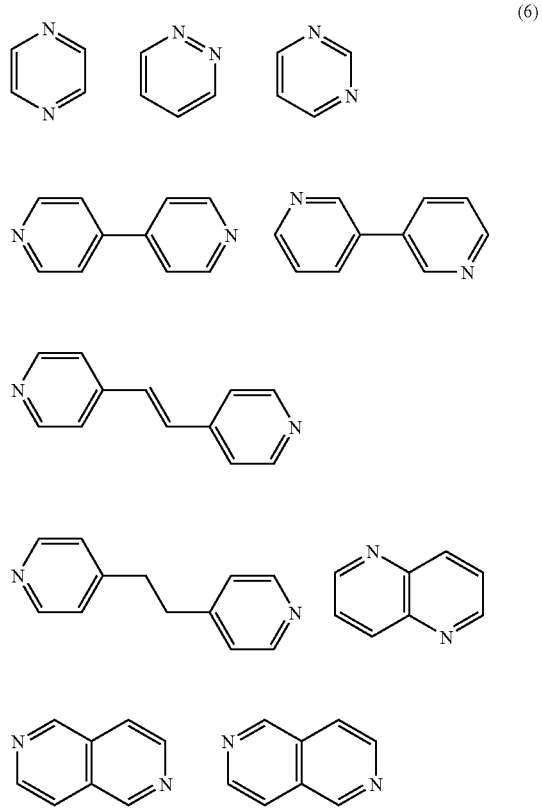

wherein a hydrogen atom in any one of the above aromatic rings may be substituted by one of a halogen atom, an alkyl group having 2 or less carbon atoms, and an alkoxyl group having 2 or less carbon atoms; and a hydrogen atom in each of the alkyl group and the alkoxyl group may be substituted by a fluorine atom.

Specific examples of the complex represented by the general formula (1), that is, a complex having a dinuclear complex structure having two metal atoms in any one of its repeating units are shown below.

Description will be given by taking Compound 101 as an example. X shown in the structural formula (a) of Compound 101 is selected from halogen elements Cl, Br, and I. In addition, $M_1$ and $M_2$ represent different metals, and are each selected from Cu, Ag, and Au. x1, y1, and z1 each represent the number of repeating structures, and the arrangement of repeating structures may be regular or irregular. x1, y1, and z1 satisfy the relationship of $50<(x1+y1+z1)<1,000,000$. Comparison between different repeating units shows that the repeating units have the same ligands and the same coordination geometry except a metal. That is, the foregoing corresponds to the fact that the metals represented by $M_1$ and $M_2$ are statistically distributed in the polymeric metal complex in accordance with a mixing ratio between the metals. Therefore, the structural formula (a) of Compound 101 can be rewritten like a structural formula 101(b). Here, M can be represented as $M=(x)M_1(1-x)M_2$ (where x represents the molar ratio of $M_1$) in accordance with a mixing ratio between $M_1$ and $M_2$. Such structure as described above can be experimentally identified by performing X-ray structure analysis after the synthesis of the compound. The structural formulae of compounds except Compound 101 shown below followed the notation of the structural formula 101(b) described above.

(101a)

-continued
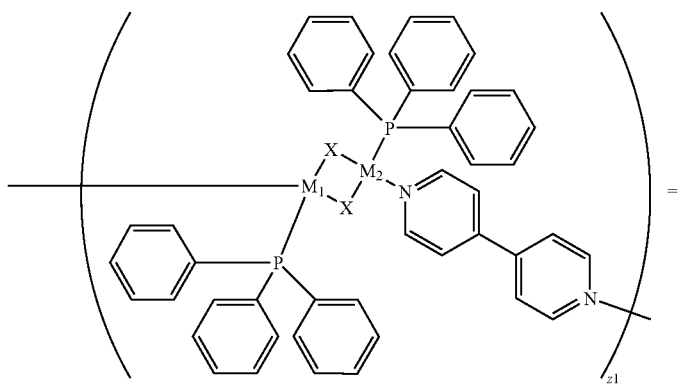
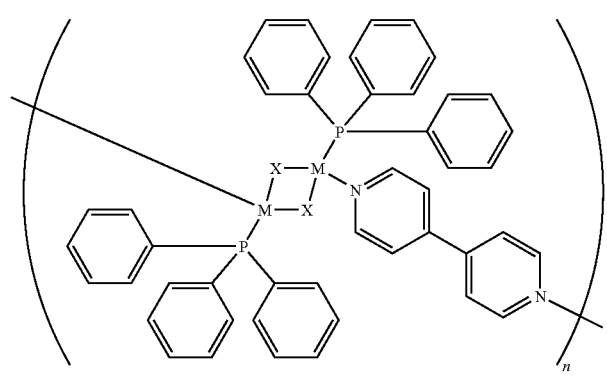
101(b)
M = $x$M$_1$(1-$x$)M$_2$
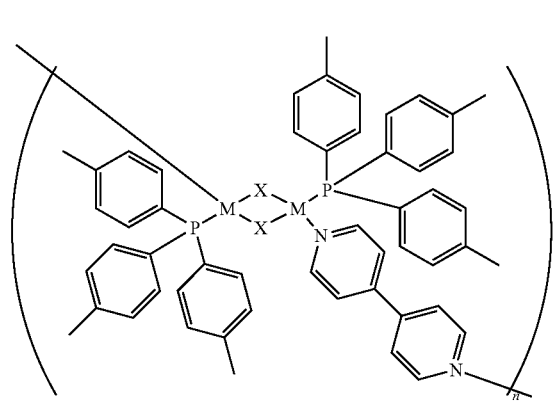
102
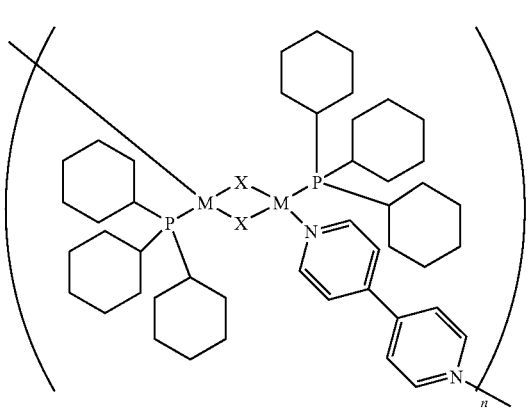
103
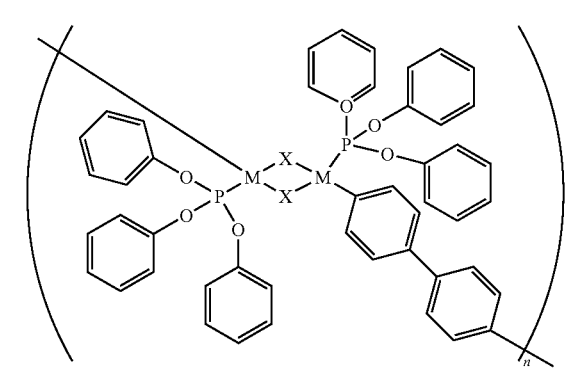
104
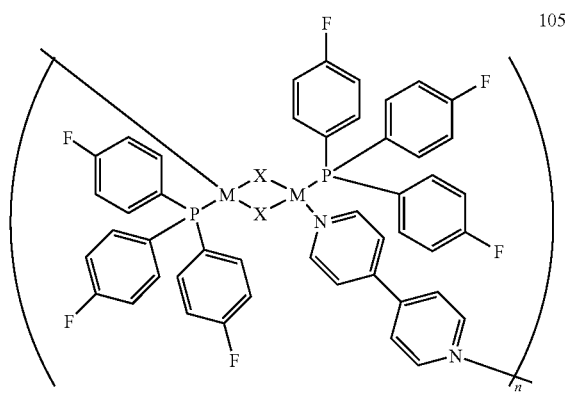
105

-continued
106
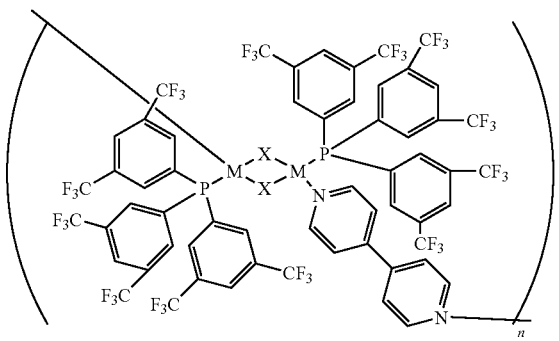
107
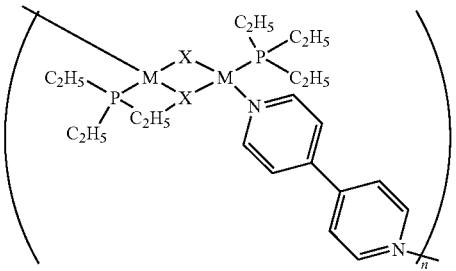
201
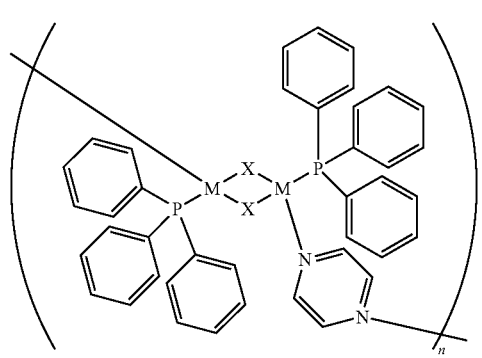
202
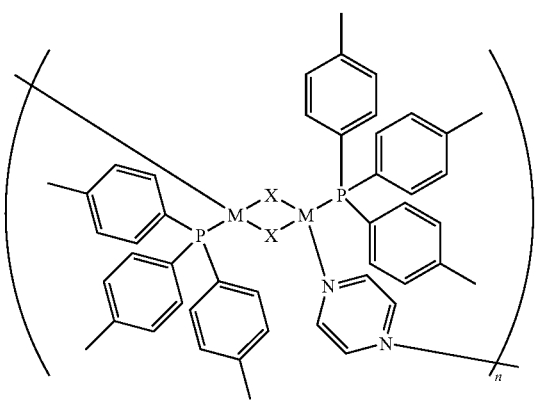
203
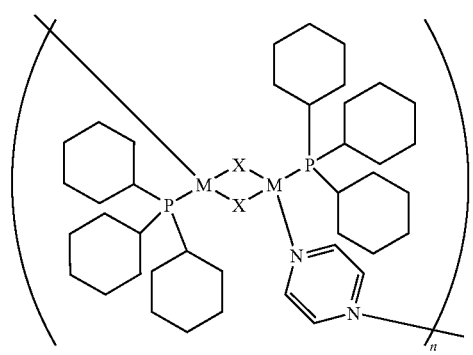
204
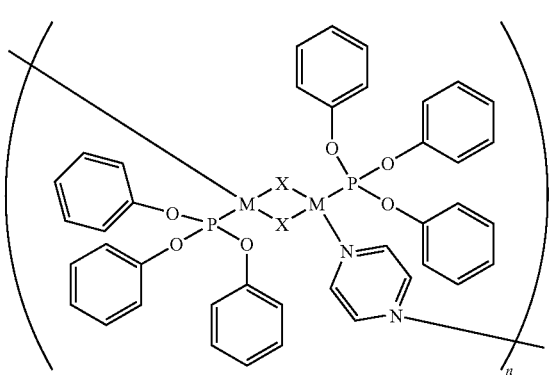
205
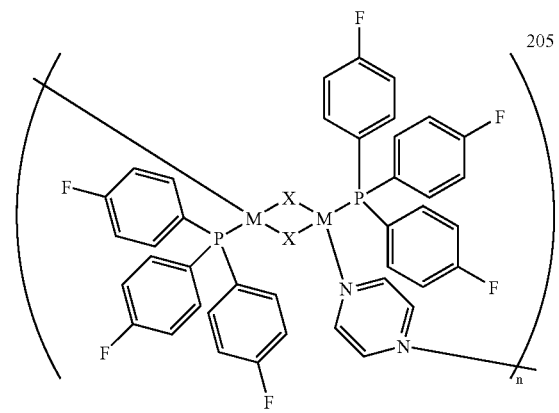
206
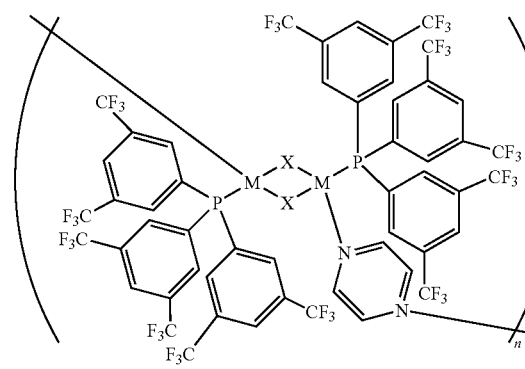

207
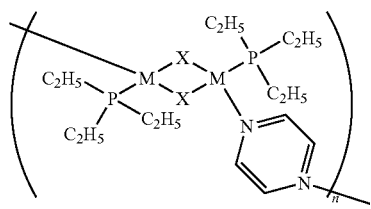
208
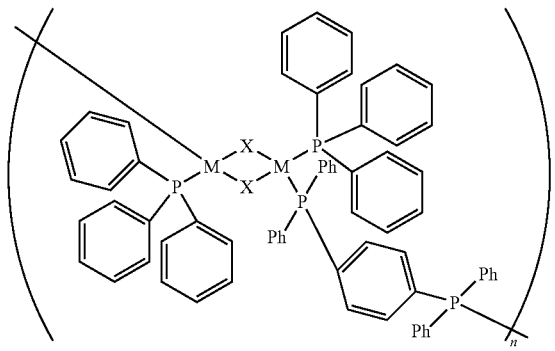
209
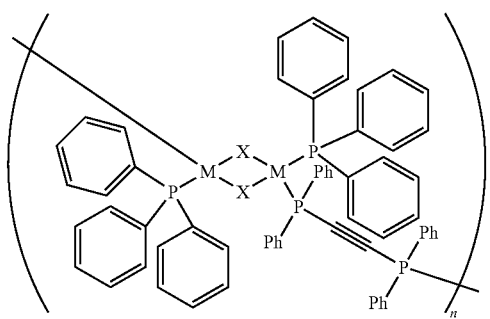
210
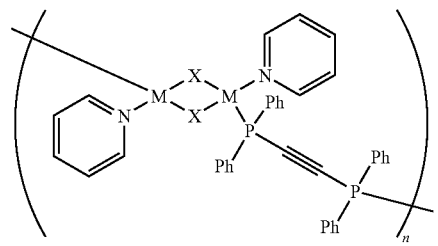
301
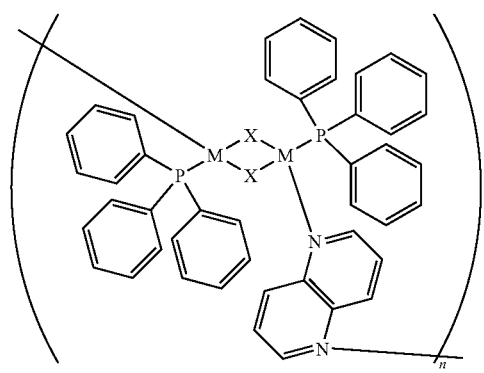
302
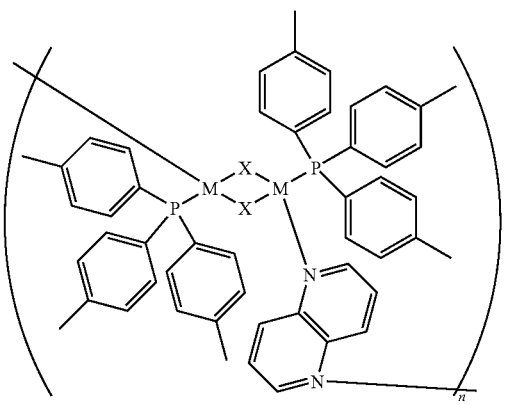

-continued
303
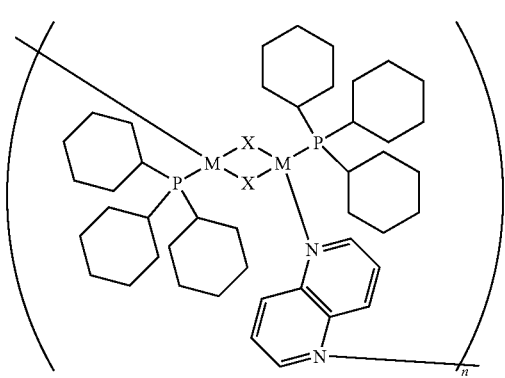
304
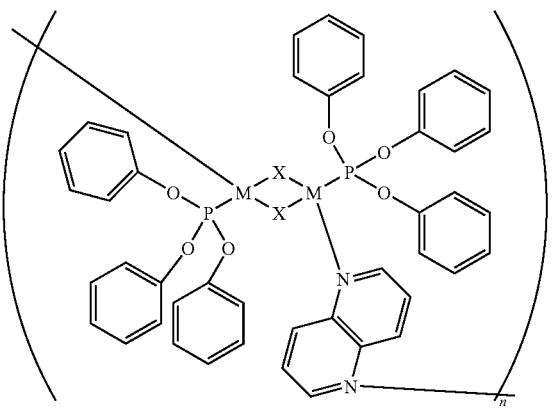
305
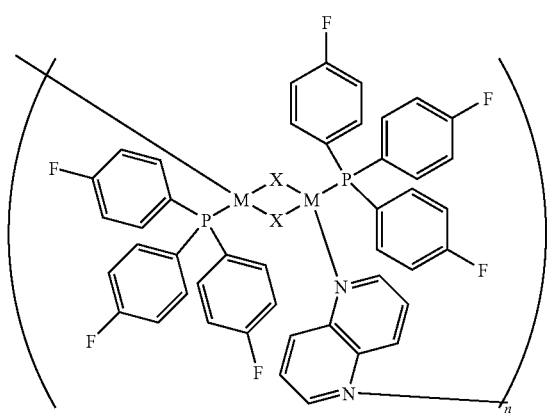
306
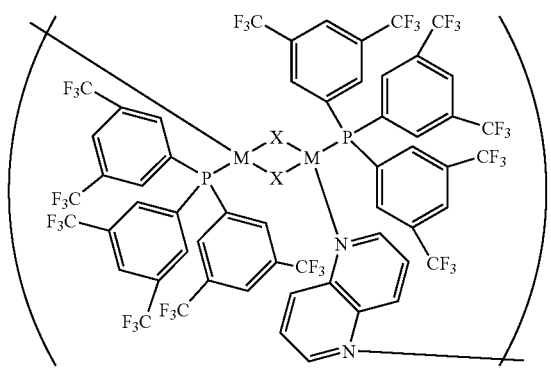
307
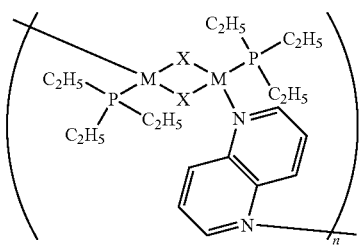
308
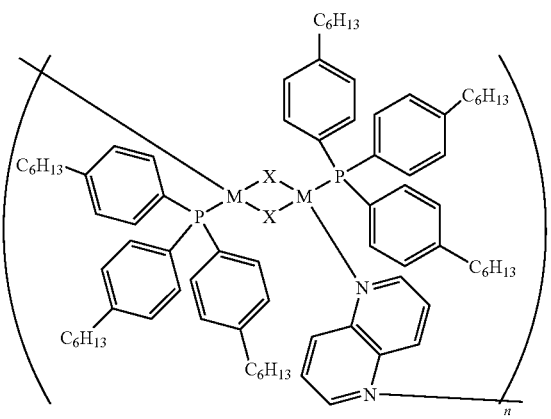

-continued

309

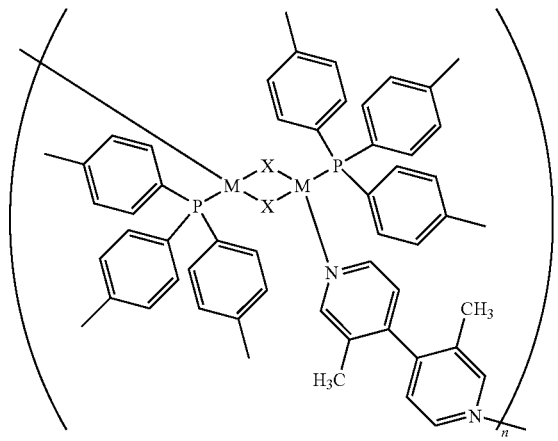

309

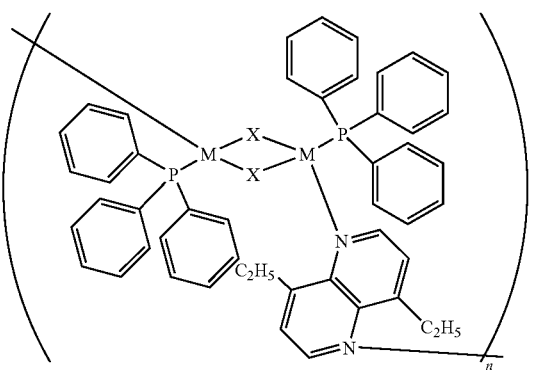

On the other hand, a complex represented by the following general formula (7) is preferably used as the complex represented by the general formula (2), and a complex represented by the following general formula (8) is more preferably used as the complex represented by the general formula (2):

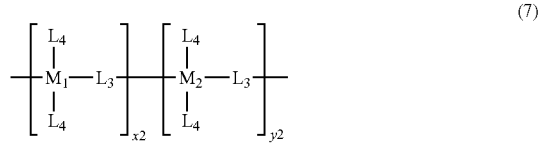
(7)

wherein $L_3$ represents a bidentate ligand, and $L_4$ represents a monodentate ligand.

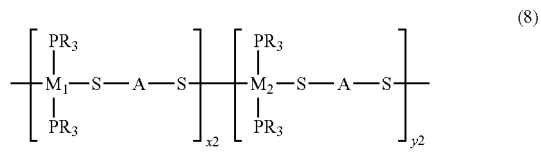
(8)

wherein $PR_3$ represents a tertiary phosphine using P as a coordinating atom, and is selected from tertiary phosphines shown in the following structural formulae (9):

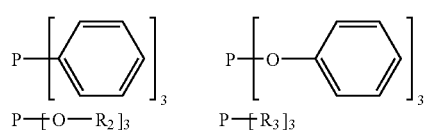
(9)

wherein: a hydrogen atom of a phenyl group may be substituted by one of a halogen atom, a branched or linear alkyl group having 10 or less carbon atoms, and a branched or linear alkoxyl group having 10 or less carbon atoms, and $R_2$ and $R_3$ each represent a linear, branched, or cyclic alkyl group having 6 or less carbon atoms; and S-A-S represents a bidentate ligand using S as a coordinating atom, and two S atoms are bonded to each other by A formed of plural covalent bonds.

Specific examples of the complex represented by the general formula (2), that is, a polymeric mixed-metal complex in which a repeating unit has a mononuclear complex structure are shown below. As in the case of the foregoing description concerning the specific examples of the complex represented by the general formula (1), notations (a) and (b) were shown for Compound 401. Compounds except Compound 401 followed the notation of 401(b).

401 (a)

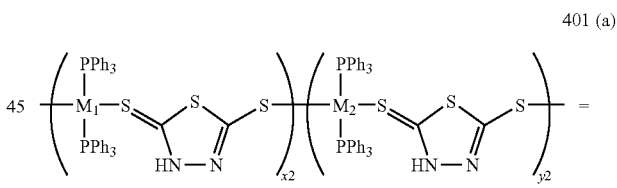

401 (b)

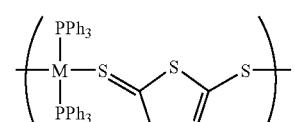

$M = xM_1(1-x)M_2$

401

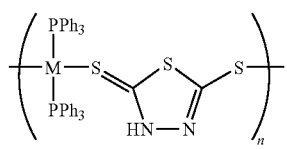

-continued

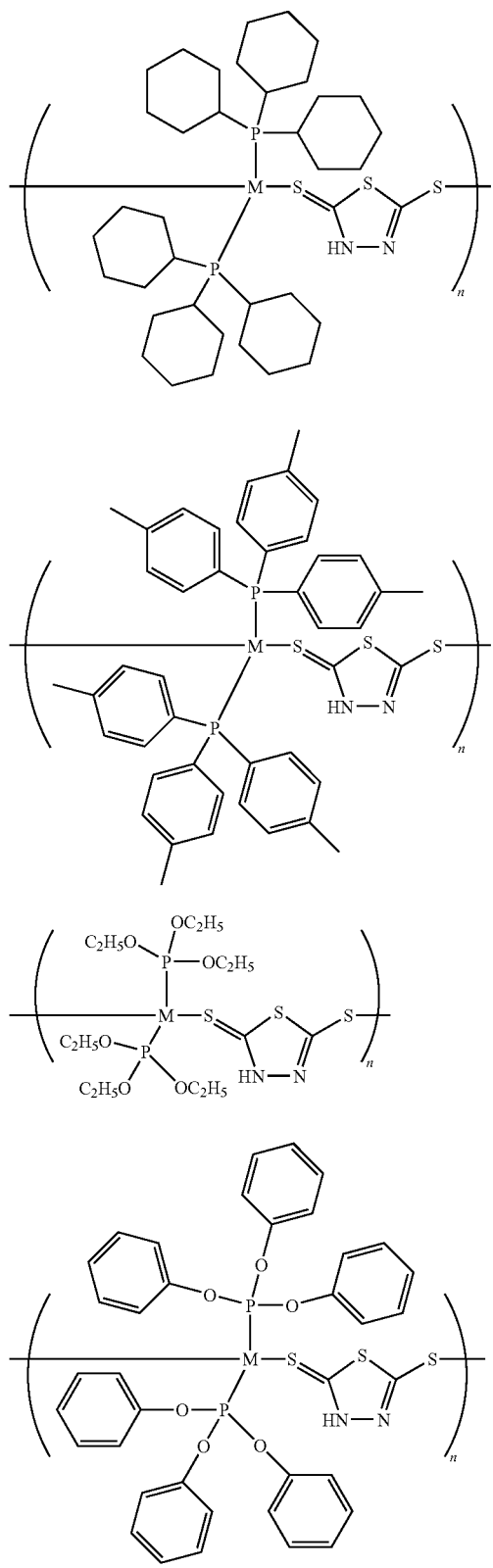

A representative example of the present invention is a polymeric mixed-metal complex having a skeleton structure shown in Compound 101. Here, M represents a mixed metal Cu(x)Ag(1−x) (where x=0.8 to 0.0001), and X represents iodine. A method of synthesizing the complex, and the molecular structural diagram of the complex provided by X-ray structure analysis are shown in an example.

Figure 2:
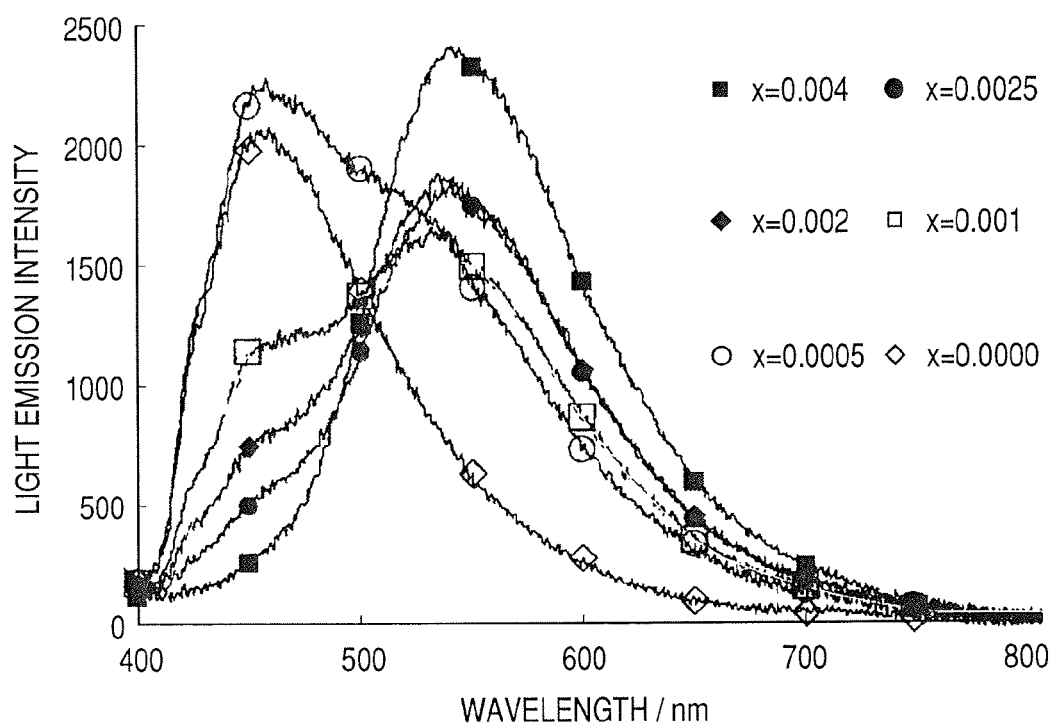
FIG. 2 is a view showing the emission spectrum of $[\{(Cu_xAg_{1-x})_2I_2(PPh_3)_2\}(bpy)]_n$.

Next, the light emitting property of the polymeric mixed-metal complex will be described. FIG. 2 shows comparison between the emission spectrum of the polymeric mixed-metal complex and the emission spectrum of a polymeric complex formed of a single metal. As shown in FIG. 2, two emission bands derived from Ag and Cu complexes (emission band of the Ag complex: 400 to 480 nm, emission band of the Cu complex: 530 to 650 nm) were observed, and it was found that the mixing of Ag and Cu resulted in the overlapping of the respective spectra of Ag and Cu. Further, even when the ratio at which copper was mixed was small, the emission band derived from the copper complex was observed, and substantially no emission band other than the emission band corresponding to the copper complex was observed for x=0.004.

Light emitted from the mixed-metal complex attenuates in a relatively complex manner when the emission band derived from the silver complex and the emission band derived from the copper complex are simultaneously observed. Table 2 to be described later summarizes data on the emission lifetime of Compound 101 in each of the emission band derived from the silver complex and the emission band derived from the copper complex. Emitted light monotonously decayed in the emission band corresponding to the silver complex (400 to 480 nm), but emitted light decayed to show a maximum for about 5 μs in the emission band corresponding to the copper complex (530 to 650 nm). The foregoing phenomenon cannot be understood when one considers that the formation of an excited state is due only to photoexcitation; the phenomenon shows that energy transfer from a silver light emitting site having a long lifetime to a copper light emitting site having a short lifetime progresses. In addition, in the example of x=0.004, light emission occurs mainly in the copper emission band; in the polymeric complex, the energy transfer progresses with high efficiency, and the excitation energy of the silver site is centralized in the copper site, whereby light is emitted.

Mixing metals as described above can provide a light emitting material capable of the following:
(1) an emission peak wavelength, that is, a luminescent color can be changed;
(2) a broad emission spectrum can be obtained, and light having a mixed color or a white color can be emitted; and
(3) a polymeric mixed-metal complex shows luminous efficiency higher than that of a polymeric single metal complex.

Although the reason why high emission quantum efficiency can be obtained is unclear, one possible reason is as follows: a new phenomenon, that is, the centralization of energy in the copper site occurs as a result of the formation of the polymeric mixed-metal complex, whereby the high quantum efficiency is obtained. In addition, a mixed-metal site such as {AgCuX$_2$} may contribute to the light emitting property of the complex.

The above-mentioned examples of a polymeric mixed-metal complex are each a polymeric metal complex containing two kinds of metals (copper and silver); a polymeric mixed-metal complex containing three kinds of metals (for example, copper, silver, and gold) is also permitted. The emission spectrum, emission yield, or the like of a polymeric mixed-metal complex containing three kinds of metals can be improved in the same manner as in a polymeric mixed-metal complex containing two kinds of metals.

The polymeric mixed-metal complex of the present invention can be applied to a light emitting device because the complex can stably emit light with high efficiency at room temperature. Since light emission is the radiant transition of excitation energy from an excited state, light emitting devices can be classified into the following devices depending on the manner in which an excited state is formed:

(1) an electroluminescence device in which a hole and an electron are coupled with each other by current excitation so that an excited state is formed;
(2) a photoluminescence device in which an excited state is formed with an excitation light source; and
(3) a cathode luminescence device in which an excited state is formed with an electron beam.

With regard to the electroluminescence device, the polymeric mixed-metal complex of the present invention can be applied to a light emitting dopant for an organic LED device. A possible example of the constitution of the organic LED device is "anode/hole injecting layer/light emitting layer/electron injecting layer/cathode", and an organic compound host in which the polymeric mixed-metal complex of the present invention is dispersed can be used in the light emitting layer. EL light emission is observed on a glass substrate side by applying a voltage of about 2 to 20 V to the device. Examples of the organic compound host are shown below.

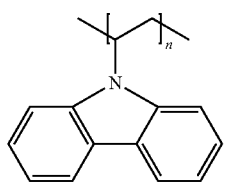
Polyvinyl
carbazole

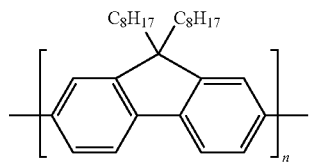
Polyfluorene

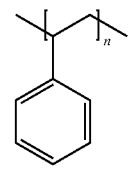
Polystyrene

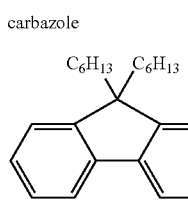
Oligofluorene
n = 4-8

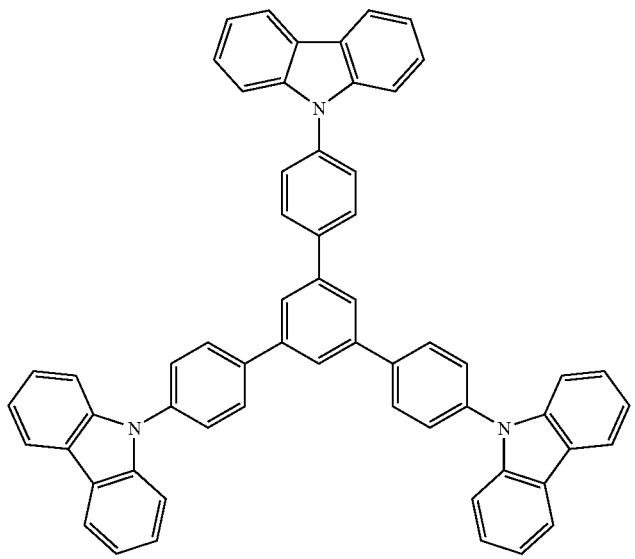
TCTB

-continued

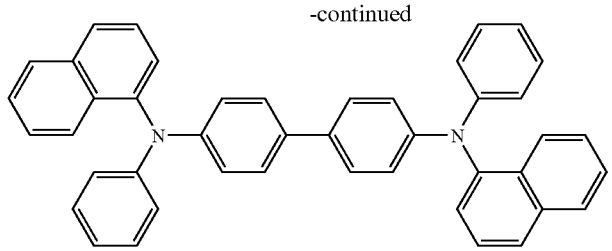

NPD

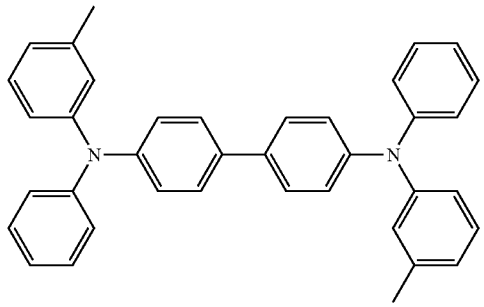

TPD

Figure 11:
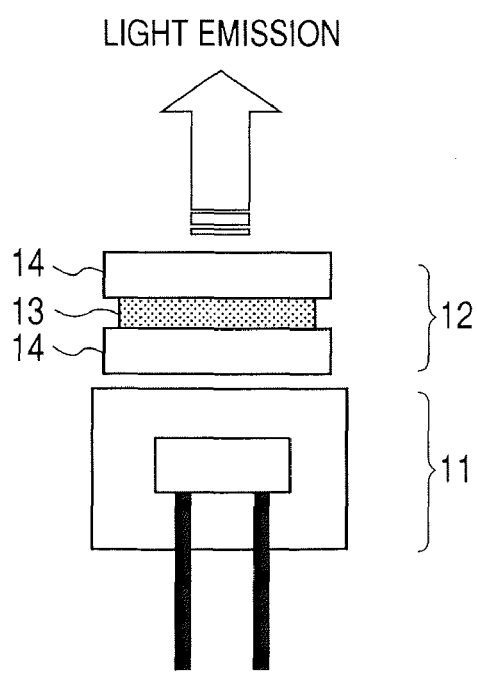
FIG. 11 is a view showing an example of the constitution of a photoluminescence device of the present invention.

The photoluminescence device can be applied to a luminescent color converting material using an organic or inorganic LED as an excitation light source. FIG. 11 shows an example of the constitution of the photoluminescence device. In the figure, reference numeral 11 represents an inorganic LED; 12, the photoluminescence device; 13, a light emitting layer; and 14, glass. For example, an electric field is applied to the inorganic LED device capable of emitting ultraviolet light, whereby ultraviolet light (having an emission peak wavelength of 250 to 400 nm) is emitted from the inorganic LED device. The photoluminescence device placed in front of the inorganic LED and having the light emitting layer containing the complex of the present invention is irradiated with light from the inorganic LED. The photoluminescence device absorbs light from the inorganic LED to form an excited state, and light emitted from the excited state is observed from the outside of the photoluminescence device.

The cathode luminescence device can be applied to, for example, a phosphor for a cathode ray tube (CRT).

EXAMPLE 1

This example relates to a polymeric mixed-metal complex represented by the structural formula 101 in which the metal M is a mixed metal Cu(x)Ag(1−x), and the halogen atom X represents iodine.

<Synthesis Method (1) $[\{(Cu_{0.5}Ag_{0.5})_2I_2(PPh_3)_2\}(bpy)]_n$ for x=0.5

AgI (12.4 mg, 0.053 mmol) and $PPh_3$ (28.5 mg, 0.109 mmol) were dissolved in 32 ml of DMF.

CuI (9.8 mg, 0.051 mmol) and $PPh_3$ (27.3 mg, 0.104 mmol) were dissolved in 8 ml of $CH_3CN$.

The two solutions were mixed with each other, whereby a colorless solution was obtained. The solution was added to a solution prepared by dissolving bpy (47.7 mg, 0.305 mmol) in about 1 ml of $CH_3CN$, and the whole was left standing while light was shielded. A yellow crystal was produced in a yield of 46.2 mg two days after the leaving.

(2) $[\{(Cu_{0.2}Ag_{0.8})_2I_2(PPh_3)_2\}(bpy)]_n$ for x=0.2

AgI (9.3 mg, 0.040 mmol), CuI (2.0 mg, 0.011 mmol), and $PPh_3$ (26.7 mg, 0.102 mmol) were dissolved in a mixed solution of DMF and $CH_3CN$ (32 ml:8 ml). The solution was added to a solution prepared by dissolving bpy (23.9 mg, 0.153 mmol) in about 1 ml of $CH_3CN$, and the whole was left standing while light was shielded. A yellow crystal was produced in a yield of 16.3 mg two days after the leaving.

(3) $[\{(Cu_{0.004}Ag_{0.996})_2I_2(PPh_3)_2\}(bpy)]_n$ for x=0.004

AgI (10.0 mg, 0.043 mmol) and $PPh_3$ (23.2 mg, 0.089 mmol) were dissolved in 30 ml of DMF.

CuI (10.2 mg, 0.054 mmol) and $PPh_3$ (28.6 mg, 0.109 mmol) were dissolved in 25 ml of $CH_3CN$, and a $CH_3CN$ solution was prepared by diluting 1 ml of the resultant solution by 100-fold with a 100-ml measuring flask.

8 ml of the solution of CuI and $PPh_3$ diluted by 100-fold were added to the solution of AgI and $PPh_3$. The resultant solution was added to a solution prepared by dissolving bpy (20 mg, about 0.13 mmol) in about 1 ml of $CH_3CN$, and the whole was left standing while light was shielded, whereby a crystal was obtained in a yield of 18.4 mg.

(4) $[\{(Cu_{0.002}Ag_{0.998})_2I_2(PPh_3)_2\}(bpy)]_n$ for x=0.002

AgI (10.0 mg, 0.043 mmol) and $PPh_3$ (23.2 mg, 0.089 mmol) were dissolved in 30 ml of DMF.

CuI (10.2 mg, 0.054 mmol) and $PPh_3$ (28.6 mg, 0.109 mmol) were dissolved in 25 ml of $CH_3CN$, and a $CH_3CN$ solution was prepared by diluting 1 ml of the resultant solution by 100-fold with a 100-ml measuring flask.

4 ml of the solution of CuI and $PPh_3$ diluted by 100-fold were added to the solution of AgI and $PPh_3$. The resultant solution was added to a solution prepared by dissolving bpy (20 mg, about 0.13 mmol) in about 5 ml of $CH_3CN$, and the whole was left standing while light was shielded, whereby a crystal was obtained in a yield of 18.2 mg.

(5) $[\{(Cu_{0.001}Ag_{0.999})_2I_2(PPh_3)_2\}(bpy)]_n$ for x=0.001

AgI (10.0 mg, 0.043 mmol) and $PPh_3$ (23.2 mg, 0.089 mmol) were dissolved in 30 ml of DMF.

CuI (10.2 mg, 0.054 mmol) and $PPh_3$ (28.6 mg, 0.109 mmol) were dissolved in 25 ml of $CH_3CN$, and a $CH_3CN$ solution was prepared by diluting 1 ml of the resultant solution by 100-fold with a 100-ml measuring flask.

2 ml of the solution of CuI and $PPh_3$ diluted by 100-fold were added to the solution of AgI and $PPh_3$. The resultant solution was added to a solution prepared by dissolving bpy (20 mg, about 0.13 mmol) in about 7 ml of $CH_3CN$, and the whole was left standing while light was shielded, whereby a crystal was obtained in a yield of 15.6 mg.

(6) $[\{(Cu_{0.0005}Ag_{0.9995})_2I_2(PPh_3)_2\}(bpy)]_n$ for x=0.0005

AgI (10.0 mg, 0.043 mmol) and $PPh_3$ (23.2 mg, 0.089 mmol) were dissolved in 30 ml of DMF.

CuI (10.2 mg, 0.054 mmol) and $PPh_3$ (28.6 mg, 0.109 mmol) were dissolved in 25 ml of $CH_3CN$, and a $CH_3CN$ solution was prepared by diluting 1 ml of the resultant solution by 100-fold with a 100-ml measuring flask.

1 ml of the solution of CuI and $PPh_3$ diluted by 100-fold were added to the solution of AgI and $PPh_3$. The resultant solution was added to a solution prepared by dissolving bpy (20 mg, about 0.13 mmol) in about 8 ml of $CH_3CN$, and the whole was left standing while light was shielded, whereby a crystal was obtained in a yield of 18.8 mg.

<Compound Identification>

The results of the elemental analysis of the resultant mixed-metal complexes are shown below. The measurement was performed with an elemental analyzer (elemental analyzer VarioEL CHNOS manufactured by Elementar). A calculated value (Calcd.) and an observed value (Obs.) coincided with each other well. The foregoing showed that a ratio between Cu and Ag in a complex was determined in accordance with a reaction equivalent ratio.

TABLE 1

| x | | C | H | N |
|---|---|---|---|---|
| $5 \times 10^{-4}$ | Calcd. | 48.03 | 3.33 | 2.44 |
| | Obs. | 47.91 | 3.40 | 2.42 |
| $1 \times 10^{-3}$ | Calcd. | 48.03 | 3.33 | 2.44 |
| | Obs. | 47.86 | 3.27 | 2.42 |
| $2 \times 10^{-3}$ | Calcd. | 48.03 | 3.33 | 2.44 |
| | Obs. | 47.90 | 3.24 | 2.45 |
| $4 \times 10^{-3}$ | Calcd. | 48.03 | 3.33 | 2.44 |
| | Obs. | 47.96 | 3.27 | 2.42 |
| $2.0 \times 10^{-1}$ | Calcd. | 48.78 | 3.38 | 2.47 |
| | Obs. | 48.57 | 3.47 | 2.17 |
| $5 \times 10^{-1}$ | Calcd. | 49.96 | 3.46 | 2.53 |
| | Obs. | 49.76 | 3.50 | 2.56 |

<X-Ray Structure Analysis>

The molecular structure of each of the mixed-metal complexes was determined by X-ray single crystal structure analysis because each of the mixed-metal complexes was obtained in the form of a single crystal. A copper single complex and a silver single complex were crystals of the same shape; the mixed-metal complexes were also crystals of the same shape, and each had a chain structure in which $\{M_2I_2(PPh_3)_2\}$ units were crosslinked with bpy as in the case of a single metal complex. Single crystal structure analysis revealed that a silver ion and a copper ion could not be distinguished from each other, so metal ions were statistically distributed in a crystal. FIG. 1 shows an ORTEP view for x=0.5.

<Emission Spectrum>

FIG. 2 shows an emission spectrum with respect to a mixing ratio between copper and silver. The alteration of the emission spectrum in accordance with the mixing ratio was attained. The emission spectrum of a mixed-metal complex showed a shape that was understandable by the overlapping of a silver single complex and a copper single complex. As a copper ratio increases, the emission spectrum of the mixed-metal complex shows the following phenomenon: the amount of a silver complex component reduces, and the amount of a copper complex component increases. The emission spectrum of the mixed-metal complex is sensitive to the amount of copper; the emission spectrum coincides with that of the copper complex when the copper ratio is 0.004.

The fact that the emission spectrum of the mixed-metal complex corresponds to the overlapping of the silver single complex and the copper single complex shows that the silver/copper light emitting site in the mixed-metal complex has the same emission energy as that of the silver/copper single complex. The selection of a crosslinking ligand may also be able to change the emission energy. In addition, the fact that the copper site emits light efficiently even when the copper ratio is small shows that energy transfer from the silver site to the copper site progresses in an extremely efficient manner.

<Emission Lifetime and Emission Quantum Efficiency>

The emission lifetime, emission maximum wavelength, and emission quantum efficiency of each of the mixed-metal complexes are shown below. The third harmonic having a wavelength of 355 nm (half width 7 ns) of Nd-YAG Laser (Continuum, Surelite II) was used as excitation light. A multichannel photodetector (Hamamatsu Photonics K.K., PMA 11) was used as a detector for spectral measurement, and a streaks camera (Hamamatsu Photonics K.K., C4334) was used as a detector for lifetime measurement. A solid powder state was subjected to measurement.

TABLE 2

| | Emission lifetime[a]/µs | |
|---|---|---|
| x | 400 nm-480 nm | 550 nm-650 nm |
| 0 | 18.7 | — |
| $5 \times 10^{-4}$ | 3.3, 16, 7 | 3.1,[b] 16.1 |
| $1 \times 10^{-3}$ | 3.3, 13.2 | 3.4,[b] 12.5 |
| $2 \times 10^{-3}$ | 2.2, 9.1 | 3.0,[b] 9.6 |
| $4 \times 10^{-3}$ | 1.4, 5.9 | 2.0,[b] 7.3 |
| $2.0 \times 10^{-1}$ | — | 5.1 |
| $5 \times 10^{-1}$ | — | 4.1 |
| 1.0 | — | 4.0 |

[a]A mixed-metal complex showed a single emission lifetime over the entire emission wavelength region for x = 0, $2.0 \times 10^{-1}$, $5 \times 10^{-1}$, or 1.0.
[b]Increased component

TABLE 3

| x | Emission maximum wavelength/nm | Emission quantum efficiency |
|---|---|---|
| 0 | 458 | 0.7 ± 0.1 |
| $5 \times 10^{-4}$ | 461 | 0.9 ± 0.1 |
| $1 \times 10^{-3}$ | 464 | 0.9 ± 0.1 |
| $2 \times 10^{-3}$ | 538 | 0.9 ± 0.1 |
| $4 \times 10^{-3}$ | 544 | 0.9 ± 0.1 |
| $2.0 \times 10^{-1}$ | 548 | 0.9 ± 0.1 |
| $5 \times 10^{-1}$ | 547 | 0.9 ± 0.1 |
| 1.0 | 547 | 0.4 ± 0.1 |

Light emitted from each of the silver and copper single complexes decayed with a single exponential function. The silver single complex had an emission lifetime of 18.7 µs, and the copper single complex had an emission lifetime of 4.0 µs. In contrast, light emitted from each of the mixed-metal complexes each serving as a compound in which an emission band inherent in a silver complex and an emission band inherent in a copper complex were simultaneously observed did not decay with a single exponential function. In each of those compounds, emitted light monotonously decayed in a portion corresponding mainly to the emission spectrum of the silver complex in the range of 400 nm to 480 nm. While emitted light showed the following behavior in a portion corresponding mainly to the emission spectrum of the copper complex in the range of 530 nm to 650 nm, that is, light emission intensity increased immediately after excitation, and then reduced. The fitting of the emission lifetimes of both emission bands was attained with two exponential functions. The resultant lifetimes of the two emission bands substantially corresponded to each other. The foregoing suggests that energy transfer should occur between the two light emitting sites.

The behavior is evident from a time-resolved spectrum. In spite of the fact that, in the case of a single complex, the silver complex shows a longer lifetime than that of the copper complex, light is emitted mainly from the silver complex immediately after the excitation, but the main site from which light is emitted shifts to the copper site with the passage of time. Such behavior shows that energy transfer progresses from the silver site to the copper site.

In a complex having a copper ratio of 0.001, the time period for which emitted light decays to show a local maximum in a portion corresponding to the light emission of a copper site is 5 µs. The time period for which emitted light shows a local maximum shortens with increasing copper ratio. This is probably because an increase in copper ratio increases the number of copper sites, whereby energy transfer from a silver site to a copper site is facilitated.

In a complex having an additionally high copper ratio, specifically, x=0.2 or 0.5, a silver site was not observed to emit light, so it was found that energy transfer to a copper site occurred with high efficiency.

A silver single complex showed an emission quantum efficiency of 0.7±0.1, and a copper single complex showed an emission quantum efficiency of 0.4±0.1. A compound having a mixing ratio between the silver and copper single complexes of 0.0005, 0.001, 0.002, 0.004, 0.2, or 0.5 showed extremely high yield, specifically, 0.9±0.1.

The polymeric mixed-metal complex of this example showed extremely high emission quantum efficiency by mixing metals.

EXAMPLE 2

This example relates to a polymeric mixed-metal complex represented by the structural formula 101 in which the metal M is a mixed metal Cu(x)Ag(1−x), and the halogen atom X represents bromine.

<Synthesis Method>

Polymeric mixed-metal complexes for x=0.5, 0.004, 0.0025, 0.002, 0.001, and 0.0005 were synthesized. A method of synthesizing the polymeric mixed-metal complex for x=0.004 will be described as a representative example.

(1) Synthesis of $[\{(Cu_{0.004}Ag_{0.996})_2Br_2 (PPh_3)_2\}(bpy)]_n$

AgBr (10.0 mg, 0.053 mmol) and PPh$_3$ (28.0 mg, 0.107 mmol) were dissolved in 30 ml of DMF.

CuBr (14.8 mg, 0.033 mmol) and PPh$_3$ (17.7 mg, 0.067 mmol) were dissolved in 25 ml of CH$_3$CN, and a CH$_3$CN solution was prepared by diluting 1 ml of the resultant solution by 50-fold with a 50-ml measuring flask.

5 ml of the solution of CuBr and PPh$_3$ diluted by 50-fold were added to the solution of AgBr and PPh$_3$. The resultant solution was added to a solution prepared by dissolving bpy (25 mg, about 0.16 mmol) in about 1 ml of CH$_3$CN, and the whole was left standing while light was shielded, whereby a crystal was obtained in a yield of 17.2 mg.

<Compound Identification>

The results of the elemental analysis of the mixed-metal complexes each subjected to measurement in the same manner as in Example 1 are shown below. A calculated value (Calcd.) and an observed value (Obs.) coincided with each other well. The foregoing showed that a ratio between Cu and Ag in a complex was determined in accordance with a reaction equivalent ratio.

TABLE 4

| x | | C | H | N |
|---|---|---|---|---|
| $5 \times 10^{-4}$ | Calcd. | 52.30 | 3.63 | 2.65 |
| | Obs. | 52.34 | 3.66 | 2.51 |
| $1 \times 10^{-3}$ | Calcd. | 52.30 | 3.63 | 2.65 |
| | Obs. | 52.17 | 3.62 | 2.49 |
| $2 \times 10^{-3}$ | Calcd. | 52.30 | 3.63 | 2.65 |
| | Obs. | 52.22 | 3.59 | 2.50 |
| $2.5 \times 10^{-3}$ | Calcd. | 52.30 | 3.63 | 2.65 |
| | Obs. | 52.26 | 3.66 | 2.69 |
| $4 \times 10^{-3}$ | Calcd. | 52.30 | 3.63 | 2.65 |
| | Obs. | 52.52 | 3.55 | 2.41 |
| $5 \times 10^{-1}$ | Calcd. | 54.60 | 3.78 | 2.77 |
| | Obs. | 54.84 | 3.71 | 2.88 |

<X-Ray Structure Analysis>

Figure 3:
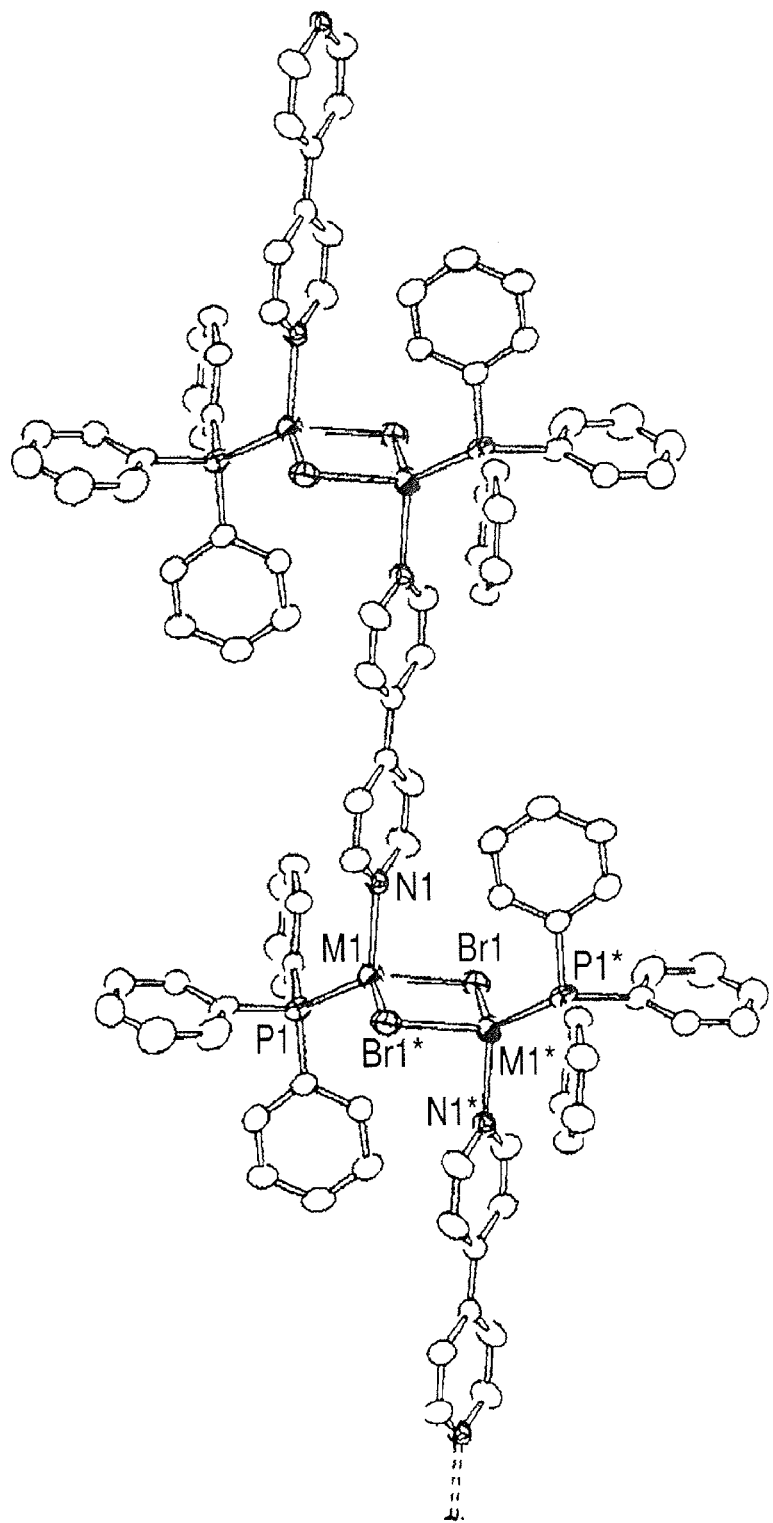
FIG. 3 is an ORTEP view of $[\{(Cu_xAg_{1-x})_2Br_2(PPh_3)_2\}(bpy)]_n$ (x=0.5).

The molecular structure of each of the mixed-metal complexes was determined by X-ray single crystal structure analysis because each of the mixed-metal complexes was obtained in the form of a single crystal. As in the Example 1, a copper single complex and a silver single complex were crystals of the same shape. The mixed-metal complexes were also crystals of the same shape, and each had a chain structure in which $\{M_2I_2(PPh_3)_2\}$ units were crosslinked with bpy as in the case of a single metal complex. FIG. 3 shows an ORTEP view for x=0.5. Single crystal structure analysis revealed that a silver ion and a copper ion could not be distinguished from each other, so metal ions were statistically distributed in a crystal.

<Emission Spectrum>

Figure 4:
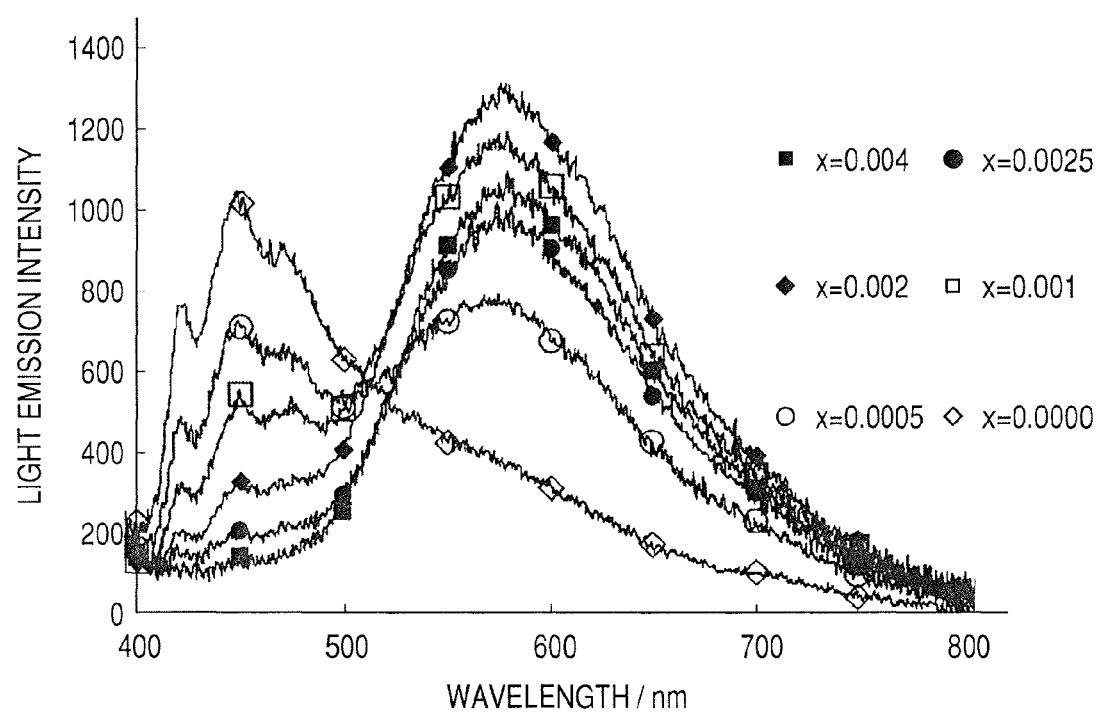
FIG. 4 is a view showing the emission spectrum of $[\{(Cu_xAg_{1-x})_2Br_2(PPh_3)_2\}(bpy)]_n$.

FIG. 4 shows an emission spectrum with respect to a mixing ratio between copper and silver. Comparison between Example 1 and Example 2 showed that an emission band derived from the light emission of a copper complex in Example 2 covered a longer wavelength range than that in Example 1 even at the same mixing ratio. As in the case of the emission spectrum shown in FIG. 2, the alteration of the emission spectrum of this example in accordance with the mixing ratio was attained. The emission spectrum of a mixed-metal complex can be described by the overlapping of a silver single complex and a copper single complex. As a copper ratio increases, the emission spectrum of the mixed-metal complex shows that the amount of a silver complex component reduces and the amount of a copper complex component increases. The emission spectrum of the mixed-metal complex is sensitive to the amount of copper and the emission spectrum coincides with that of the copper complex when the copper ratio is 0.004.

The fact that the emission spectrum of the mixed-metal complex corresponds to the overlapping of the silver single complex and the copper single complex shows that the silver/copper light emitting site in the mixed-metal complex has the same emission energy as that of the silver/copper single complex. In addition, the selection of a crosslinking ligand may also be able to change the emission energy. In addition, the fact that the copper site emits light efficiently even when the copper ratio is small shows that energy transfer from the silver site to the copper site progresses in an extremely efficient manner.

<Emission Quantum Efficiency>

The emission maximum wavelength and emission quantum efficiency of each of the mixed-metal complexes are shown below. While a single metal complex showed a quantum efficiency of about 0.4, each mixed-metal complex showed a quantum efficiency of about 0.5. The foregoing showed that each mixed-metal complex was a system the quantum efficiency of which increased as a result of the mixing of metals as in the case of Example 1.

TABLE 5

| x | Emission maximum wavelength/nm | Emission quantum efficiency |
|---|---|---|
| 0 | 447 | 0.42 ± 0.1 |
| $5 \times 10^{-4}$ | 569 | 0.49 ± 0.1 |
| $1 \times 10^{-3}$ | 572 | 0.49 ± 0.1 |
| $2 \times 10^{-3}$ | 579 | 0.47 ± 0.1 |
| $2.5 \times 10^{-3}$ | 582 | 0.49 ± 0.1 |
| $4 \times 10^{-1}$ | 578 | 0.50 ± 0.1 |
| 1.0 | 573 | 0.46 ± 0.1 |

EXAMPLE 3

This example relates to a polymeric mixed-metal complex represented by the structural formula 401 in which the metal M is a mixed metal Cu(x)Ag(1−x).

<Synthesis Method>$[Cu_xAg_{1-x}(PPh_3)_2(DMcTH)]_n$

Complexes having the same shape in each of which two metal(I) ions were mixed were synthesized by applying the fact that compounds having the same composition were obtained by using a copper(I) DMcT complex and a silver(I) DMcT complex.

CuCl (0.1xx mmol) and PPh$_3$ (72.0 mg, 0.30 mmol) were dissolved in DMF (5 ml), and DMcTH$_2$ (15.0 mg, 0.10 mmol) dissolved in a small amount of DMF was dropped to the solution. A solution of AgNO$_3$ (0.1×(1−x) mmol) in DMF was dropped to the resultant solution, and the whole was left standing in a dark room. Synthesis was performed while a value for x was changed to 0.1, 0.3, 0.5, 0.7, and 0.9. The reaction solution changed from a colorless solution to a nearly yellow solution as the value for x increased. A crystal obtained from the solution also changed from a colorless crystal to a nearly yellow crystal as the value for x increased. The yield of each polymeric mixed-metal complex is shown below.

TABLE 6

| x | Yield (mg) |
|---|---|
| 0.1 | 34.9 |
| 0.3 | 44.5 |
| 0.5 | 50.5 |
| 0.7 | 25.4 |
| 0.9 | 16.7 |

<Compound Identification>

The results of the elemental analysis of the mixed-metal complexes each subjected to measurement in the same manner as in Example 1 are shown below. A calculated value (Calcd.) and an observed value (Obs.) coincided with each other well. The foregoing showed that a ratio between Cu and Ag in a complex was determined in accordance with a reaction equivalent ratio.

TABLE 7

| x | | C | H | N |
|---|---|---|---|---|
| 0.1 | Calcd. | 61.53 | 4.21 | 3.78 |
| | Obs. | 61.71 | 4.518 | 3.66 |
| 0.3 | Calcd. | 60.80 | 4.16 | 3.73 |
| | Obs. | 61.18 | 4.42 | 3.60 |
| 0.5 | Calcd. | 60.09 | 4.11 | 3.69 |
| | Obs. | 60.42 | 4.45 | 3.54 |
| 0.7 | Calcd. | 59.40 | 4.07 | 3.65 |
| | Obs. | 59.91 | 4.31 | 3.54 |
| 0.9 | Calcd. | 58.72 | 4.02 | 3.60 |
| | Obs. | 58.98 | 4.11 | 3.54 |

<X-Ray Structure Analysis>

Figure 5:
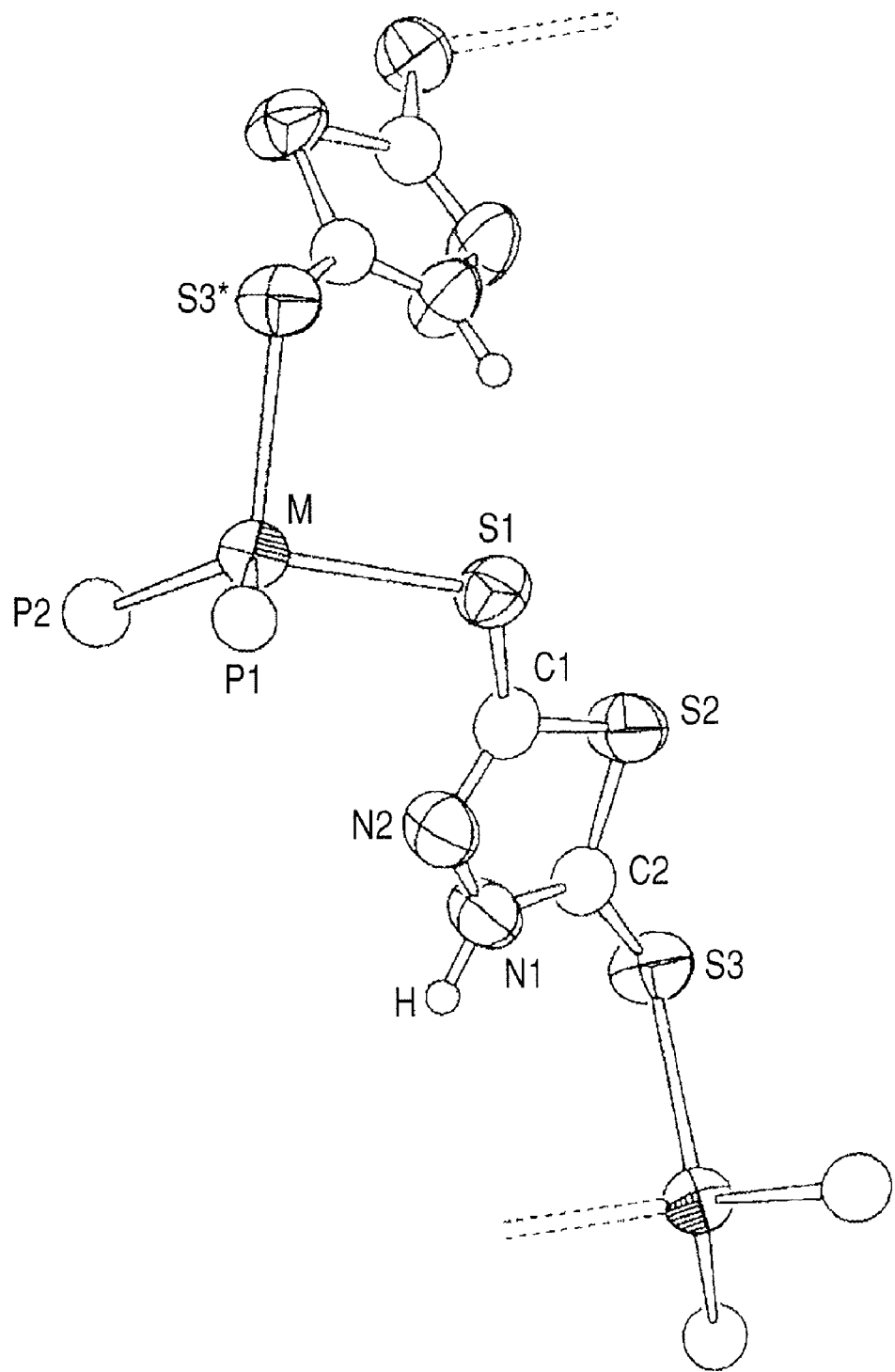
FIG. 5 is an ORTEP view of $[Cu_xAg_{1-x}(PPh_3)_2(DMcTH)]_n$ (x=0.1).

All compounds were each obtained in the form of a single crystal. The crystal structure of each of those compounds was determined with a single crystal X-ray diffractometer (a system obtained by combining an AFC-7S or an AFC-8R and a Mercury CCD detector). It was found that all crystals had the same shape, and copper and silver were statistically distributed to crystallographically equivalent sites. All crystals were each found to have a one-dimensional infinite chain structure in which $\{M(I)(PPh_3)_2\}$ (M=Ag, Cu) units were crosslinked with a monovalent anion DMcTH$^-$. FIG. 5 shows the ORTEP view of a polymeric mixed-metal complex for x=0.1.

<Emission Spectrum>

Figure 6:
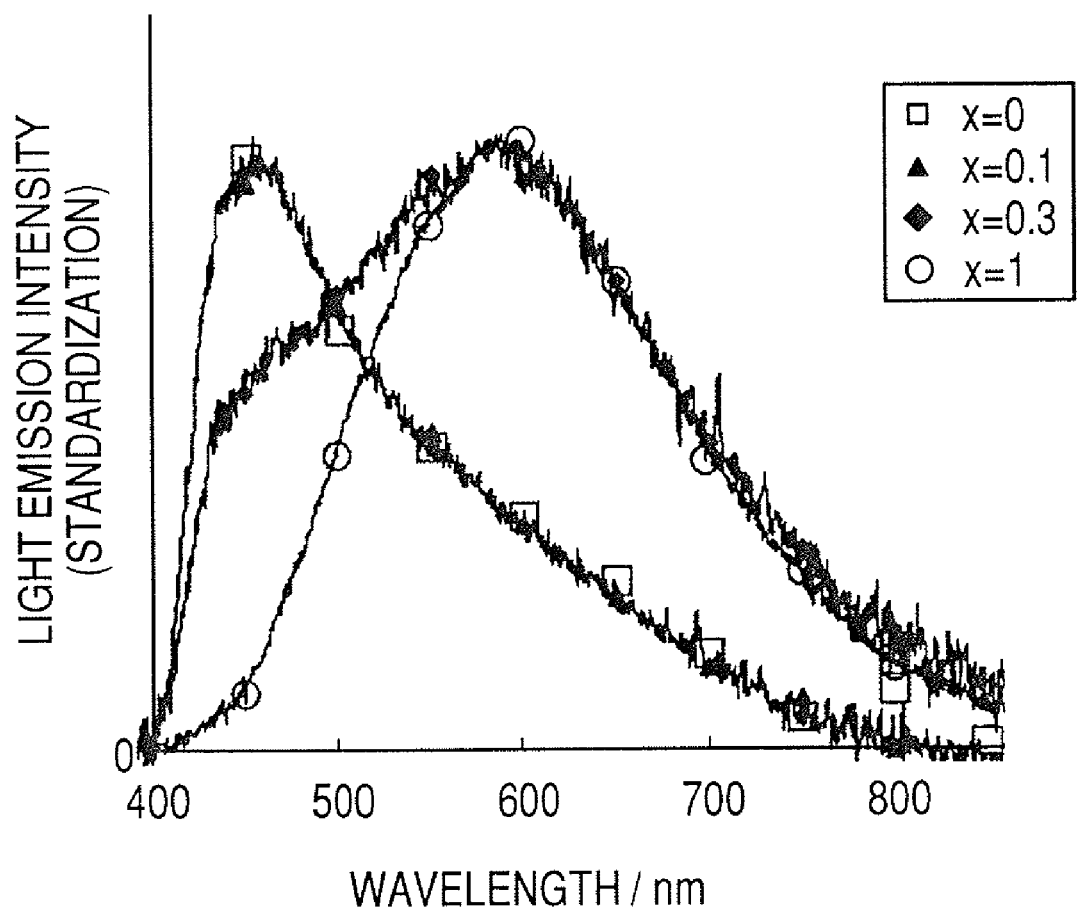
FIG. 6 is a view showing the emission spectrum of $[Cu_xAg_{1-x}(PPh_3)_2(DMcTH)]_n$.

FIG. 6 shows the emission spectrum of each of compounds for x=0, 0.1, 0.3, and 1. As in the case of each of Examples 1 and 2, each compound was observed to show an emission spectrum considered to result from the overlapping of single complexes. It was found that changing a copper or silver ratio was able to change the emission spectrum, and to control the luminescent color, of each compound.

EXAMPLE 4

This example relates to a polymeric mixed-metal complex represented by the structural formula 401 in which the metal M is a mixed metal Au(x)Ag(1−x).

<Synthesis Method>

(1) $[Au_{0.1}Ag_{0.9}(PPh_3)_2(DMcTH)]_n$

A molecular complex of gold [Au(PPh$_3$)$_2$(DMcTH)] (29.1 mg, 0.03 mmol) and AgNO$_3$ (5.7 mg, 0.03 mmol) were dissolved in DMF (30 ml). PPh$_3$ (26.9 mg, 0.10 mmol) was dissolved in DMF (5 ml), and the solution was dropped to the above solution. Subsequently, DMcTH$_2$ (6.1 mg, 0.03 mmol) was dissolved in DMF (5 ml), and the solution was dropped to the above mixture. A pale yellow crystal was obtained from the colorless reaction solution in a yield of 12.3 mg.

(2) $[Au_{0.3}Ag_{0.7}(PPh_3)_2(DMcTH)]_n$

AgNO$_3$ (3.5 mg, 0.02 mmol) was dissolved in DMF (5 ml). PPh$_3$ (12.2 mg, 0.05 mmol) was dissolved in DMF (5 ml), and the solution was dropped to the above solution. Subsequently, DMcTH$_2$ (3.1 mg, 0.02 mmol) was dissolved in DMF (5 ml), and the solution was dropped to the above mixture. The resultant was dropped to a solution of a molecular complex of gold [Au(PPh$_3$)$_2$(DMcTH)] (35.9 mg, 0.04 mmol) in acetone. The resultant was concentrated to about 5 ml with an evaporator. A yellow crystal was obtained from the solution in a yield of 20.2 mg.

<Compound Identification>

Each compound was subjected to elemental analysis.

[$Au_{0.1}Ag_{0.9}(PPh_3)_2(DMcTH)$]$_n$ Calcd; C, 57.73; H, 3.95; N, 3.5. Obs.; C, 57.74; H, 3.92; N, 3.61

[$Au_{0.3}Ag_{0.7}(PPh_3)_2(DMcTH)$]$_n$ Calcd; C, 56.46; H, 3.87; N, 3.47. Obs.: C, 56.50; H, 4.10; N, 3.68

Unlike a Cu—Ag mixed-metal complex of Example 3, the content of gold was smaller than a reaction equivalent ratio. A possible reason for the foregoing is that a gold complex can be present as a mononuclear complex having good solubility, so the gold complex remains as a molecular complex in a solution.

<X-Ray Structure Analysis>

Figure 7:
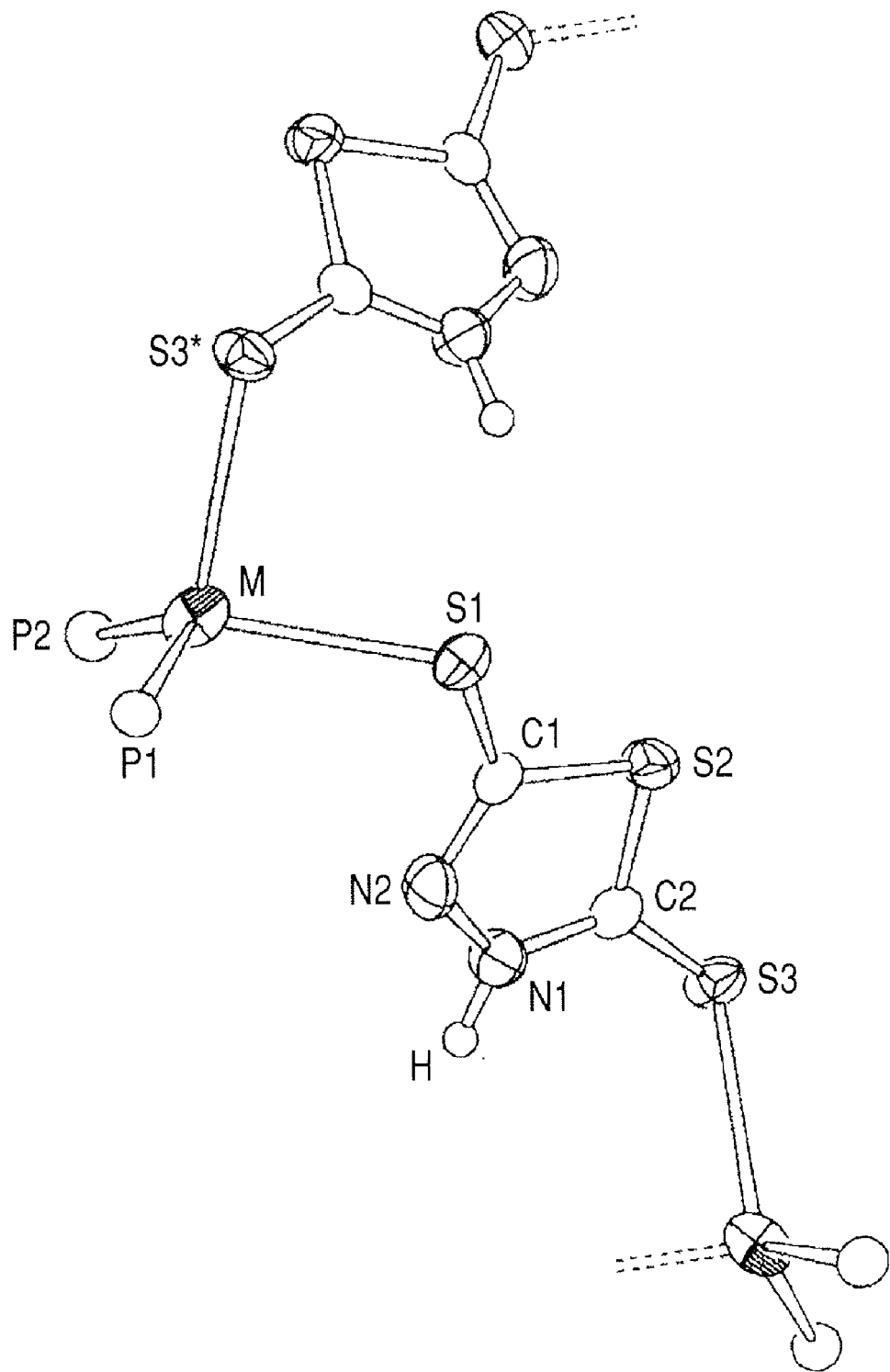
FIG. 7 is an ORTEP view of $[Au_xAg_{1-x}(PPh_3)_2(DMcTH)]_n$ (x=0.3).

All compounds were each obtained in the form of a single crystal. The crystal structure of each of those compounds was determined in the same manner as in Example 3. It was found that all crystals had the same shape, and gold and silver were statistically distributed to crystallographically equivalent sites. All crystals were each found to have a one-dimensional infinite chain structure in which {$M(I)(PPh_3)_2$} (M=Au, Ag) units were crosslinked with a monovalent anion DMcTH$^-$. FIG. 7 shows the ORTEP view of a polymeric mixed-metal complex for x=0.3.

<Emission Spectrum>

Figure 8:
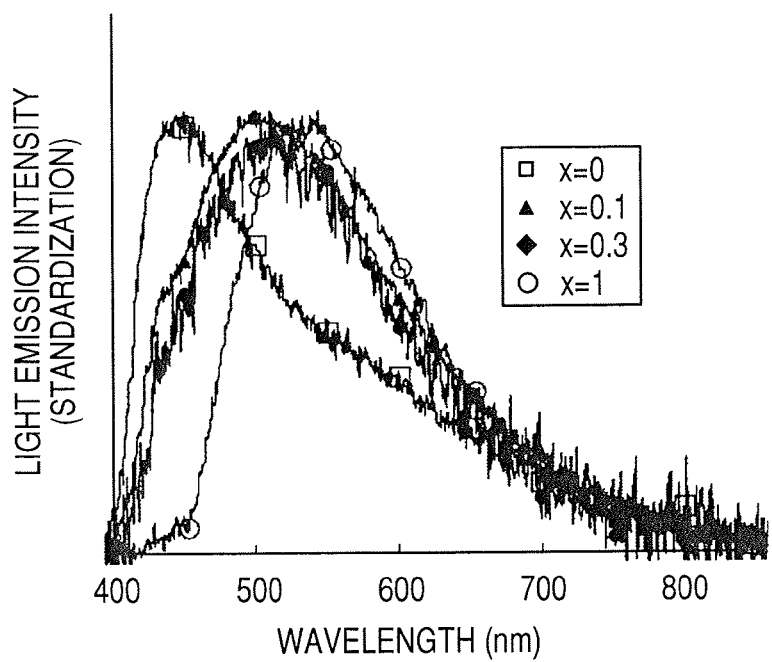
FIG. 8 is a view showing the emission spectrum of $[Au_xAg_{1-x}(PPh_3)_2(DMcTH)]_n$.

FIG. 8 shows the emission spectrum of each of compounds for x=0, 0.1, 0.3, and 1. As in the case of each of Examples 1 and 2, each compound was observed to show an emission spectrum considered to result from the overlapping of single complexes. It was found that changing a gold or silver ratio was able to change the emission spectrum, and to control the luminescent color, of each compound.

EXAMPLE 5

The polymeric mixed-metal complexes (x=0, 0.0005, 0.002, and 0.004) synthesized in Example 1 were each ground with a mortar to have a reduced particle diameter. After that, 1 mg of the ground product was dispersed in 100 cc of chloroform under stirring. 1 mg of polymethyl methacrylate was separately dissolved in 100 cc of chloroform, and the solution and the above solution were mixed at 1:1. The mixture was dropped onto a washed glass substrate, and the whole was dried under an ordinary environment for 1 hour.

Figure 9:
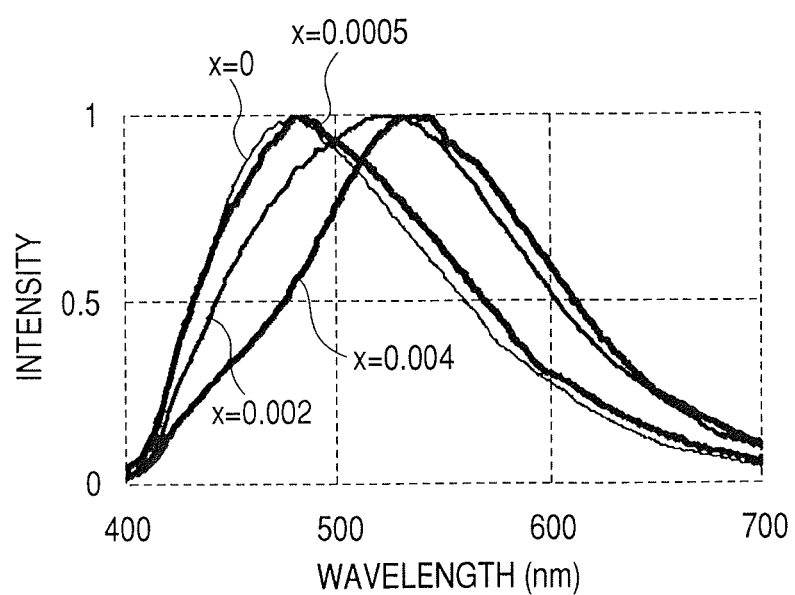
FIG. 9 is a view showing the emission spectrum of a light emitting device produced in Example 5.

When the thin film formed of the mixture was irradiated with ultraviolet light having a wavelength of 355 nm from a UV lamp, the thin film was observed to emit light uniformly. FIG. 9 shows the emission spectrum of the thin film. The light emission is light emission derived from the metal complex synthesized in Example 1. Emitted light did not decay significantly even after irradiation with excitation light for 1 hour, so light was stably emitted. The foregoing result showed that the use of the polymeric mixed-metal complex of the present invention allowed the production of a light emitting device capable of stably emitting light under an ordinary environment.

Further, the possibility that an image was formed as a result of arbitrary addressing by using the polymeric mixed-metal complex of the present invention was confirmed. The light emission of the complex was observed by scanning the complex with laser light in which the diameter of a light flux was set to 0.5 mm. As a result, the complex was observed to emit light in accordance with the laser light flux. Therefore, it was revealed that image formation was attained with the polymeric mixed-metal complex of the present invention formed into a thin film by scanning the thin film at a high speed.

EXAMPLE 6

A thin film was formed in the same manner as in Example 5 except that the polymeric mixed-metal complex synthesized in Example 3 (x=0.1) was used as a polymeric mixed-metal complex.

Figure 10:
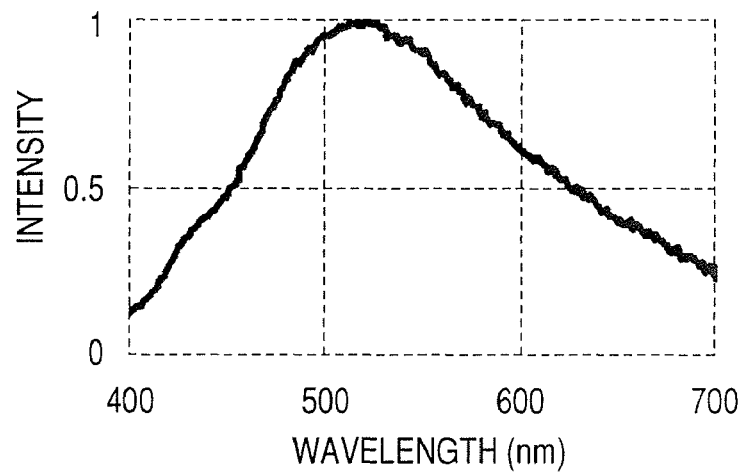
FIG. 10 is a view showing the emission spectrum of a light emitting device produced in Example 6.

When the thin film produced in this example was irradiated with ultraviolet light having a wavelength of 355 nm from a UV lamp, the thin film was observed to emit light uniformly. FIG. 10 shows the emission spectrum of the thin film. Emitted light did not decay significantly even after irradiation with excitation light for 1 hour, so light was stably emitted. The foregoing result showed that the use of the polymeric mixed-metal complex of the present invention allowed the production of a device which was stable under an ordinary environment.

Further, in the same manner as in Example 5, the light emission of the complex was observed by scanning the complex with laser light in which the diameter of a light flux was set to 0.5 mm. As a result, the complex was observed to emit light in accordance with the laser light flux. Therefore, it was revealed that image formation was attained with the polymeric mixed-metal complex of the present invention formed into a thin film by scanning the thin film at a high speed. The foregoing revealed the potential of the complex to find applications in light emitting devices.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-241147, filed Sep. 6, 2006, which is hereby incorporated by reference herein in its entirety.

What is claimed is:

1. A polymeric mixed-metal complex represented by the formula:

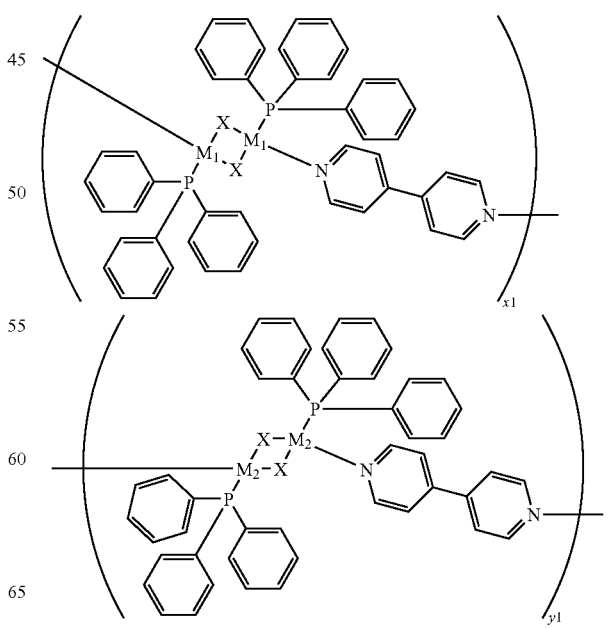

-continued

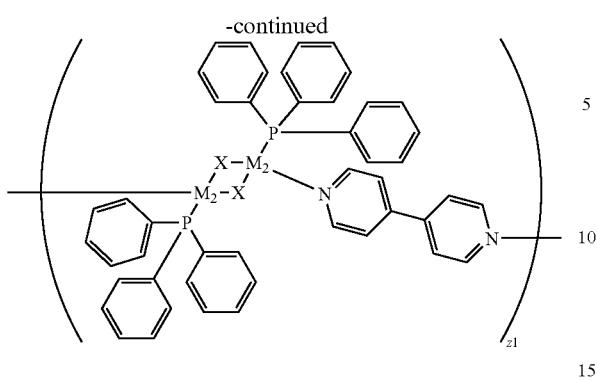

where X is I; $M_1$ is Cu; $M_2$ is Ag; the molar ratio of $M_1$ is $5\times10^{-4}$ to $4\times10^{-3}$; x1, y1, and z1 each represent the number of repeating structures, an arrangement of the repeating structures may be one of a regular arrangement and an irregular arrangement, and x1, y1, and z1 satisfy a relationship of $50<(x1+y1+z1)<1,000,000$.

2. A photoluminescence device comprising:

a pair of opposed light-transmitting members; and a light emitting layer provided between the light-transmitting members and comprising the polymeric mixed-metal complex according to claim 1, wherein the light emitting layer emits light by absorbing ultraviolet light passing through one of the light-transmitting members from an excitation light source, and emitting the light through the other light-transmitting member.

* * * * *